US012703851B2

(12) United States Patent
Yoon et al.

(10) Patent No.: US 12,703,851 B2
(45) Date of Patent: Aug. 11, 2026

(54) CELL CULTURE METHODS

(71) Applicant: The University of Massachusetts, Boston, MA (US)

(72) Inventors: Seongkyu Yoon, Lowell, MA (US); Bingyu Kuang, Worcester, MA (US); Duc Hoang, Burnsville, MN (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 973 days.

(21) Appl. No.: 17/671,029

(22) Filed: Feb. 14, 2022

(65) Prior Publication Data

US 2022/0204919 A1 Jun. 30, 2022

Related U.S. Application Data

(63) Continuation-in-part of application No. PCT/US2020/046330, filed on Aug. 14, 2020.

(60) Provisional application No. 62/886,683, filed on Aug. 14, 2019.

(51) Int. Cl.

| | |
|---|---|
| ***C12N 5/00*** | (2006.01) |
| ***C12N 5/071*** | (2010.01) |
| ***G01J 3/44*** | (2006.01) |
| ***G01N 30/72*** | (2006.01) |
| *G01N 30/02* | (2006.01) |

(52) U.S. Cl.

CPC ......... *C12N 5/0025* (2013.01); *C12N 5/0018* (2013.01); *C12N 5/0602* (2013.01); *G01J 3/44* (2013.01); *G01N 30/7206* (2013.01); *C12N 2500/32* (2013.01); *G01N 2030/027* (2013.01)

(58) Field of Classification Search

None

See application file for complete search history.

(56) References Cited

U.S. PATENT DOCUMENTS

| | | | | |
|---|---|---|---|---|
| 11,542,523 | B2 | 1/2023 | Matsuura et al. | |
| 2014/0099666 | A1* | 4/2014 | Rossomando | C12N 15/111 435/68.1 |
| 2016/0060660 | A1* | 3/2016 | Hiller | C12N 9/88 435/252.32 |
| 2017/0107552 | A1* | 4/2017 | Hiller | C12N 5/0682 |
| 2018/0265904 | A1 | 9/2018 | Hiller et al. | |
| 2019/0323020 | A1* | 10/2019 | Deng | C12N 9/1096 |
| 2022/0325235 | A1 | 10/2022 | Yoon et al. | |
| 2024/0093248 | A1 | 3/2024 | Hiller et al. | |

FOREIGN PATENT DOCUMENTS

| | | | |
|---|---|---|---|
| JP | 2018527009 | A | 9/2018 |
| WO | 2015140708 | A1 | 9/2015 |
| WO | 2015189352 | A1 | 12/2015 |
| WO | 2019117136 | A1 | 6/2019 |
| WO | 2021030672 | A1 | 2/2021 |

OTHER PUBLICATIONS

Klasson, Thomas. The Inhibitory Effects of Aconitic Acid on Bioethanol Production. Sugar Tech (Jan.-Feb. 2018) 20(1):88-94. (Year: 2018).*

Costa, Andre. Exploration of the non-conventional yeast I. orientalis as a host for itaconic acid production. (Year: 2017).*

Mulukutla, BC, et al., Metabolic engineering of Chinese hamster ovary cells towards reduced biosynthesis and accumulation of novel growth inhibitors in fed-batch cultures, Metabolic Engineering, 54, Feb. 23, 2019, pp. 54-68.

International Search Report and Written Opinion for PCT/US2023/062467 Dated Aug. 14, 2023.

Costa, A. "Exploration of the non-conventional yeast I. orientalis as a host for itaconic acid production," Master of Science Degree in Biotechnology these, Tecnico Lisboa; available online at https://fenix.tecnico.lisboa.pt/downloadFile/1689244997258332/Final%20MSc%20Thesis%20-Fenix%20Upload-%20Andre%20Costa.pdf [retrieved on Oct. 15, 2020]; Nov. 2017; pp. 1-65.

International Search Report mailed Nov. 13, 2020; International Application No. PCT/US2020/046330; International Filing Date Aug. 14, 2020 (4 pgs).

Kim et al., "Down-regulation of lactate dehydrogenase-A by siRNAs for reducted lactic acid formation of Chinese hamster ovary cells producing thrombopoietin," Appl Microbiol Biotechnol (2007) 74:152-159.

Klasson, et al., "The Inhibitory Effects of Aconitic Acid on Bioethanol Production," Sugar Tech, (2017) vol. 20, (88-94).

Muliukutla, B., et al. (2017) "Identification and control of novel growth inhibitors in fed-batch cultures of Chinese hamster ovary cells," Biotechnology and Bioengineering 114.8: 1780-1790.

Park, et al., "Development of an efficient cytosolic isobutanol production pathway in *Saccharomyces cerevisiae* by optimizing copy Nos. and expression of the pathway genes based on the toxic effect of α-acetolactate," Scientific Reports, (2019) vol. 9, No. 3996 (1-11).

Perieria, S., et al. "Impact of CHO Metabolism on Cell Growth and Protein Production: An Overview of Toxic and Inhibiting Metabolites and Nutrients," Biotechnology Journal, (2018) 13(3), 1700499; 13 pages.

Written Opinion mailed Nov. 13, 2020; International Application No. PCT/US2020/046330; International Filing Date Aug. 14, 2020 (5 pgs).

(Continued)

*Primary Examiner* — Nghi V Nguyen

(74) *Attorney, Agent, or Firm* — CANTOR COLBURN LLP

(57) ABSTRACT

A method of cell culture includes (i) culturing cells in a cell culture medium, and (ii) maintaining at least one metabolite below an inhibitory concentration in the cell culture medium for the at least one metabolite, wherein the at least one metabolite is aconitic acid (AA), leucinic acid (HICA), cytidine monophosphate (CMP), methylsuccinic acid (MSA), trigonelline (TRI), N-acetylputrescinium (NAP), or a combination thereof, and wherein the enzyme comprises ADH5, BCAT1, CAT, GOT1, HADHB, HOGA1, SLC35A1, or a combination thereof.

20 Claims, 23 Drawing Sheets

Specification includes a Sequence Listing.

(56) References Cited

OTHER PUBLICATIONS

Baerends et al., "Impaired Uptake and/or Utilization of Leucine by *Saccharomyces cerevisiae* is Suppressed by the SPT15-300 Allele of the TATA-Binding Protein Gene". Applied and Environmental Microbiology. Oct. 2009. 17 (9):6055-6061.
Ehling et al., "Investigation of the Presence of B-Hydroxy-B-methylbutyric Acid & a-Hydroxyisocaproic Acid in Bovine Whole Milk & Ferm. Daily Products by a Validated Liquid Chromatography-Mass Spectrometry Method". J. Agric. Food Chem. Feb. 2014. 62:1506-11.
Nowaczyk et al., "Ethylmalonic and Methylsuccinic Aciduria in Ethylmalonic Encephalopathy Arise From Abnormal Isoleucine Metabolism". Metabolism. Jul. 1998. 47(7):836-839.
Notice of Refusal issued Aug. 6, 2024 by the Japan IP Office in corresponding Japan patent application No. 2022-508866, with English translation, 6 pages.
PCT International Preliminary Report on Patentability issued Aug. 20, 2024 for PCT/US2023/062467, 7 pages.
Charis-P. Segeritz, Ludovic Vallier, Chapter 9—Cell Culture: Growing Cells as Model Systems In Vitro, Editor(s): Morteza Jalali, Francesca Y.L. Saldanha, Mehdi Jalali, Basic Science Methods for Clinical Researchers, Academic Press, 2017, pp. 151-172, ISBN 9780128030776, https://doi.org/10.1016/B978-0-12-803077-6.00009-6.
Narendranath NV, Power R. Relationship between pH and medium dissolved solids in terms of growth and metabolism of lactobacilli and *Saccharomyces cerevisiae* during ethanol production. Appl Environ Microbiol. May 2005;71 (5):2239-43.
Bae et al., "Alcohol Dehydrogenase 5 is a Source of Formate for De Novo Purine Biosynthesis in HepG2 Cells1-4," The Journal of Nutrition, 147(4):499-505, First published online Feb. 22, 2017; 7 pages.
Liu Mei, "GS-CHO, Optimization of Cell Culture Processes," Full Text of Outstanding Master's Thesis in China Database: Engineering Technology I, 2013, No. 03, B016-198, Jun. 3, 2012; 54 pages, Machine Translation of Sections Provided in the Foreign Action.
Kim et al., "Characterization of (R)-2-Hydroxyisocaproate Dehydrogenase and a Family III Coenzyme A Transferase Involved in Reduction of L-Leucine to Isocaproate by Clostridium difficile", Applied and Environmental Microbiology, vol. 72, No. 9, Sep. 2006; pp. 6062-6069.
Klasson, "The Inhibitory Effects of Aconitic Acid on Bioethanol Production," Sugar Tech, 20(1):88-94, Jan.-Feb. 2018; 7 pages.
Kuang et al., "Metabolic engineering of Bcat1, Adh5 and Hahdb towards controlling metabolic inhibitors and improving performance in CHO cell-cultures," Biochemical Engineering Journal, 206 (2024) 109282; 11 pages.
Lee et al., "Low-Glutamine Fed-Batch Cultures of 293-HEK Serum-Free Suspension Cells for Adenovirus Production," Biotechnol. Prog., 2003, 19, pp. 501-509.
Office Action for the Chinese Application No. 202080071742.7, Dated: Nov. 25, 2025; 8 pages, no English translation.
Office Action for the Korean Application No. 10-2022-7008312, Dated: Dec. 1, 2025; 7 pages, English translation.
Sebag et al., ADH5-mediated NO bioactivity maintains metabolic homeostasis in brown adipose tissue, Cell Reports, 37(7):110003, 2021; 20 pages.
Supplementary Partial European Search Report for the European Application No. 23753734, Dated: Feb. 3, 2026; 15 pages.
Wu et al., "A Novel Suppressive Effect of Alcohol Dehydrogenase 5 in Neuronal Differentiation*," The Journal of Biological Chemistry, vol. 289, No. 29, Jul. 18, 2014; pp. 20193-20199.
Eden et al., "Involvement of branched-chain amino acid aminotransferase (Bcat1/Eca39) in apoptosis," FEBS Letters, 457 (1999) 255-261.
Pereira et al., "BCAT1 and BCAT2 disruption in CHO cells has cell line-dependent effects," Journal of Biotechnology, 306 (2019) 24-31.
Shafei et al., "BCATc modulates crosstalk between the PI3K/ Akt and the Ras/ERK pathway regulating proliferation in triple negative breast cancer," Oncotarget, 2020, vol. 11, No. 21, pp. 1971-1987.
Supplementary European Search Report for European Patent Application No. 2375374.5, Dated: Apr. 21, 2026; 21 pages.

* cited by examiner

FIG. 11

Intensity_MC_Ch02

| Population | Count | %Gated | Mean | Median | Std. Dev. |
|---|---|---|---|---|---|
| Single_C1 & Focus | 9876 | 100 | 7995.7 | 1990.29 | 16176.82 |
| M1 & Single_C1 & Focus | 3479 | 35.2 | 19775.75 | 9965.53 | 22984.39 |

Intensity_MC_Ch02

| Population | Count | %Gated | Mean | Median | Std. Dev. |
|---|---|---|---|---|---|
| Single_C1 & Focus | 11547 | 100 | 8801.08 | 2580.19 | 16621.93 |
| M1 & Single_C1 & Focus | 4973 | 43.1 | 17518.82 | 8171.76 | 22394.07 |

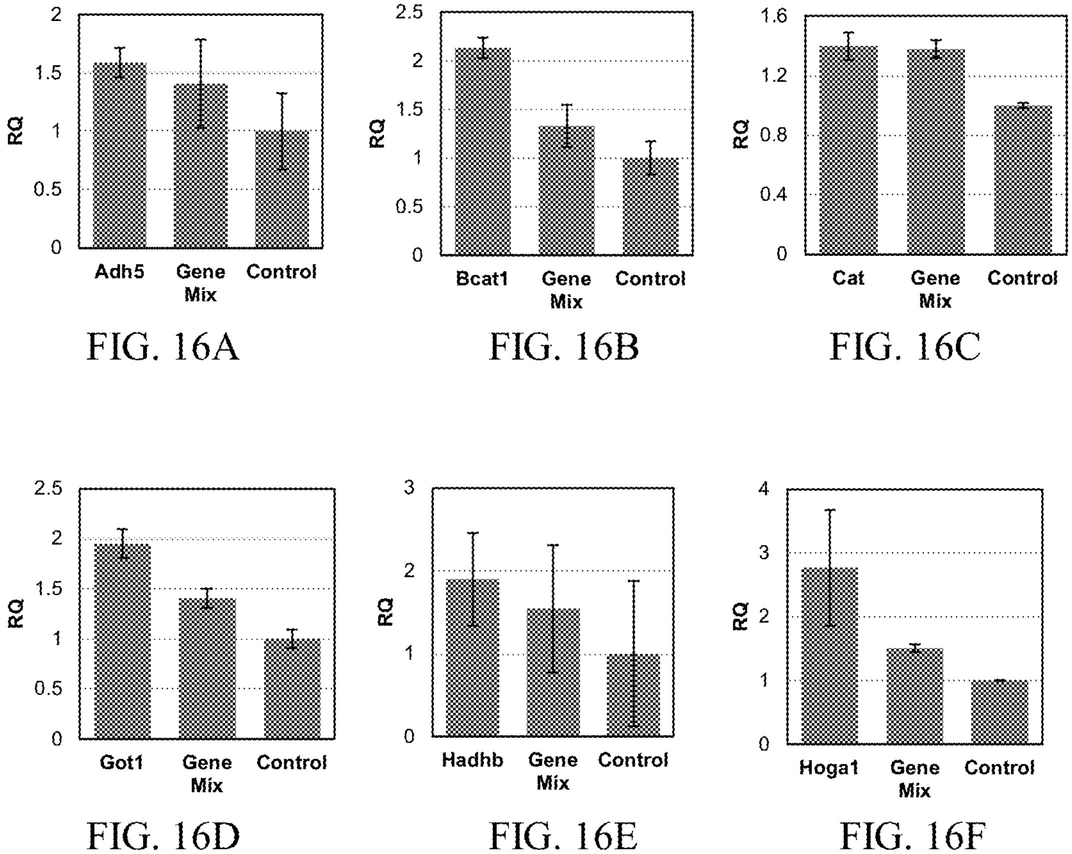
FIG. 16A
FIG. 16B
FIG. 16C
FIG. 16D
FIG. 16E
FIG. 16F
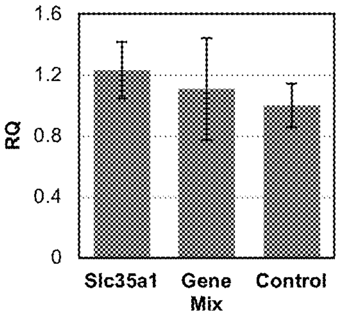
FIG. 16G

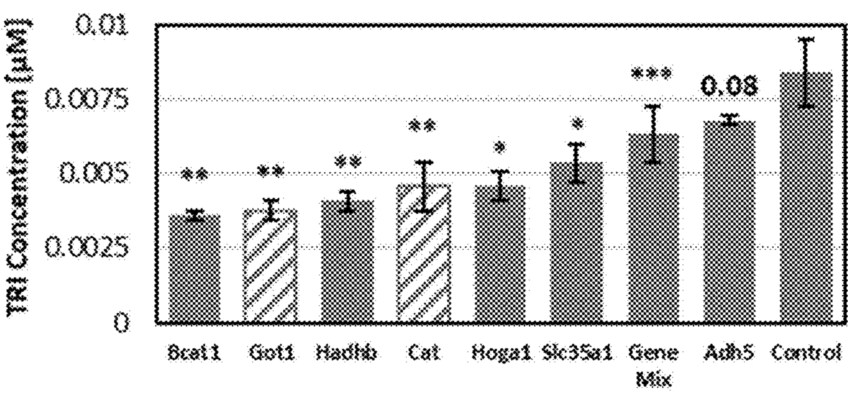
FIG. 17G
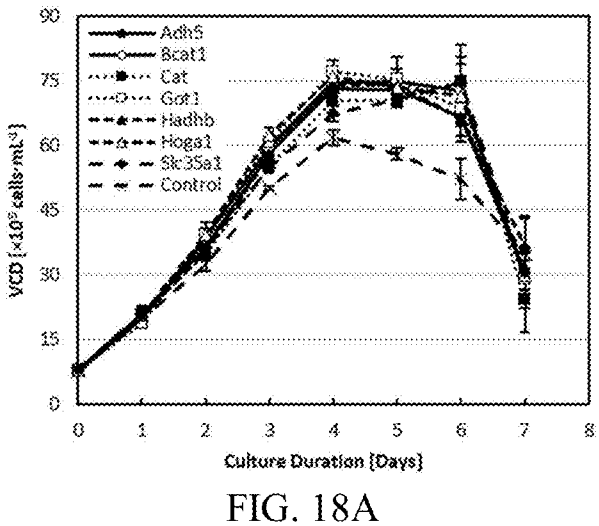
FIG. 18A
IVCD [×10⁵ cells·mL⁻¹]
450
360
270
180
90
0
0 1 2 3 4 5 6 7 8
Culture Duration [Days]
FIG. 18B

SEQUENCE LISTING

```
<160> NUMBER OF SEQ ID NOS: 14

<210> SEQ ID NO 1
<211> LENGTH: 38
<212> TYPE: DNA
<213> ORGANISM: Artificial Sequence
<220> FEATURE:
<223> OTHER INFORMATION: Adh5 forward primer

<400> SEQUENCE: 1

taatatatac ttaaggccac catggcgaac caggtgat                              38


<210> SEQ ID NO 2
<211> LENGTH: 30
<212> TYPE: DNA
<213> ORGANISM: Artificial sequence
<220> FEATURE:
<223> OTHER INFORMATION: Adh5 reverse primer

<400> SEQUENCE: 2

cggccggaat tcttacagct ttagaacagt                                       30


<210> SEQ ID NO 3
<211> LENGTH: 32
<212> TYPE: DNA
<213> ORGANISM: Artificial sequence
<220> FEATURE:
<223> OTHER INFORMATION: Bcat1 forward primer

<400> SEQUENCE: 3

taatacttaa ggccaccatg gactgcagta at                                    32


<210> SEQ ID NO 4
<211> LENGTH: 27
<212> TYPE: DNA
<213> ORGANISM: Artificial sequence
<220> FEATURE:
<223> OTHER INFORMATION: Bcat1 reverse primer

<400> SEQUENCE: 4

gcccgaattc tcacgataac aagattg                                          27


<210> SEQ ID NO 5
<211> LENGTH: 33
<212> TYPE: DNA
<213> ORGANISM: Artificial sequence
<220> FEATURE:
<223> OTHER INFORMATION: Cat forward primer

<400> SEQUENCE: 5

atatcttaag gccaccatga tgcgatttct tac                                   33


<210> SEQ ID NO 6
<211> LENGTH: 32
<212> TYPE: DNA
<213> ORGANISM: Artificial sequence
<220> FEATURE:
```

<223> OTHER INFORMATION: Cat reverse primer

<400> SEQUENCE: 6
gcgccgtcta gattatcaca ggttagcttt tt 32

<210> SEQ ID NO 7
<211> LENGTH: 33
<212> TYPE: DNA
<213> ORGANISM: Artificial sequence
<220> FEATURE:
<223> OTHER INFORMATION: Got1 forward primer

<400> SEQUENCE: 7
atacttaagg ccaccatgtc gcctccgtca gtc 33

<210> SEQ ID NO 8
<211> LENGTH: 35
<212> TYPE: DNA
<213> ORGANISM: Artificial sequence
<220> FEATURE:
<223> OTHER INFORMATION: Got1 reverse primer

<400> SEQUENCE: 8
ggcgctctag attatcactg gattttggtg acagc 35

<210> SEQ ID NO 9
<211> LENGTH: 35
<212> TYPE: DNA
<213> ORGANISM: Artificial sequence
<220> FEATURE:
<223> OTHER INFORMATION: Hadhb forward primer

<400> SEQUENCE: 9
tatacttaag gccaccatgt ctaccatctt gactt 35

<210> SEQ ID NO 10
<211> LENGTH: 28
<212> TYPE: DNA
<213> ORGANISM: Artificial sequence
<220> FEATURE:
<223> OTHER INFORMATION: Hadhb reverse primer

<400> SEQUENCE: 10
ccggaattct cattttggat aagcttcc 28

<210> SEQ ID NO 11
<211> LENGTH: 35
<212> TYPE: DNA
<213> ORGANISM: Artificial sequence
<220> FEATURE:
<223> OTHER INFORMATION: Hoga1 forward primer

<400> SEQUENCE: 11
atatcttaag gccaccatgc taggccccca gatgt 35

<210> SEQ ID NO 12
<211> LENGTH: 35
<212> TYPE: DNA
<213> ORGANISM: Artificial sequence
<220> FEATURE:
<223> OTHER INFORMATION: Hoga1 reverse primer

<400> SEQUENCE: 12
gcgctctaga ttatcagagc cagccattgt tgctg 35

-continued

```
<210> SEQ ID NO 13
<211> LENGTH: 42
<212> TYPE: DNA
<213> ORGANISM: Artificial sequence
<220> FEATURE:
<223> OTHER INFORMATION: Slc35a1 forward primer

<400> SEQUENCE: 13

tatataccca agcttgccac catggctcag gcgagagaaa at                  42


<210> SEQ ID NO 14
<211> LENGTH: 34
<212> TYPE: DNA
<213> ORGANISM: Artificial sequence
<220> FEATURE:
<223> OTHER INFORMATION: Slc35a1 reverse primer

<400> SEQUENCE: 14

gcgcgcgctc tagattatca cacaccaatg actc                           34
```

CELL CULTURE METHODS

CROSS-REFERENCE TO RELATED APPLICATIONS

This application is a bypass continuation-in-part of PCT/US2020/046330 filed on Aug. 14, 2020, which claims priority to U.S. Provisional Application 62/886,683 filed on Aug. 14, 2019, each of which is incorporated herein by reference in its entirety.

STATEMENT REGARDING FEDERALLY SPONSORED RESEARCH & DEVELOPMENT

This invention was made with government support under 1624718 awarded by the National Science Foundation. The government has certain rights in the invention.

FIELD OF THE DISCLOSURE

The present disclosure is related to cell culture methods, the production of proteins such as monoclonal antibodies in mammalian cells, novel biomarkers, and methods of control of protein production using the novel biomarkers.

BACKGROUND

Mammalian cells such as Chinese hamster ovary (CHO) and human embryonic kidney (HEK) 293 cell lines are used as hosts for producing therapeutic biologics in the biopharmaceutical industry. In the process of antibody production, CHO cells, for example, exhibit inefficient and poorly regulated metabolism as they tend to use much of the available nutrients to produce waste metabolites rather than the required amount for their growth. In the late stage of the bioprocess, the cells stop growing and stop producing antibodies, even though the nutrient levels are sufficient to support growth and protein production. The accumulated metabolites during the process are one of the major rate limiting reasons in cell proliferation and antibody production. In order to control the metabolism and increase the productivity of mammalian cells, it is crucial to identify the inhibitory waste metabolites and study their pathways.

What is needed is the identification of inhibitory metabolites and control strategy development.

BRIEF SUMMARY

In one aspect, a method of cell culture comprises (i) culturing cells in a cell culture medium, and (ii) maintaining at least one metabolite below an inhibitory concentration in the cell culture medium for the at least one metabolite, wherein the at least one metabolite is aconitic acid (AA), leucinic acid (HICA), cytidine monophosphate (CMP), methylsuccinic acid (MSA), trigonelline (TRI), N-acetylputrescinium (NAP), or a combination thereof, and wherein the enzyme comprises ADH5, BCAT1, CAT, GOT1, HADHB, HOGA1, SLC35A1, or a combination thereof.

BRIEF DESCRIPTION OF THE DRAWINGS

FIG. 11 shows cell growth profiles after upregulating regulatory enzymes for production of the inhibitory metabolites. Control indicates a CHO K1 batch cell culture control condition without transfecting any genes. T1 indicates the cell growth profile with Got1 transfected into CHO K1 cell line. T2 indicates Got1 and Hoga1 transfection. T3 indicates Got1, Hoga1, Cat, and Slc35a1 transfection. A dramatic increase in peak cell density was observed after the transfection, whereas the peak cell density was increased 50.9% in T2 and T3 compared to the control.

FIG. 13A shows up-regulation of Cat through the metabolism of tryptophan and de novo synthesis of nicotinamide. FIG. 13B shows up-regulation of Got1 and Hoga1 through the metabolism of proline. FIG. 13C shows the up-regulation of Got1 through TCA cycle. FIG. 13D shows the up-regulation of Slc35a1 through the biosynthesis pathway of N-glycan. Accumulation of inhibitors can be controlled by upregulating the expression of characterized genes (italic) responsible for modulation of metabolic enzymes that catalyze reaction.

FIG. 16A-G are graphs showing the expression levels of seven different studied genes through transfection in CHO-S cells. The study was divided into nine unique subclone groups. Each subclone was overexpressed with an individual gene of interest via transient transfection at a plasmid concentration of 50 $\mu g \cdot \mu L^{-1}$ to cells, with an additional gene mix subclone group where all seven genes were transfected to cells at once, but at lower individual plasmid concentration used in the individual case (6.25 $\mu g \cdot \mu L^{-1}$ per gene, total of plasmid concentration of 43.75 $\mu g \cdot \mu L^{-1}$ for seven genes). A negative control was included in where no plasmid transfection occurred. Each subclone was cultured for 6 days, at which time cells and cell culture supernatant were collected. Cells for both the control and transfection subclones were derived from the same culture to eliminate variation in growth cycle and other culture conditions. Gene expression levels were quantified through qPCR.

FIG. 17A-G are graphs showing inhibitory metabolite accumulation in different subclones. Accumulation concentration of metabolites shown here: FIG. 17A, CMP; FIG. 17B, GMP; FIG. 17C, HICA, FIG. 17D, MSA, FIG. 17E, NAP, FIG. 17F, TAA; and FIG. 17G, TRI. The study was divided into nine unique subclone groups. Each subclone was overexpressed with an individual gene of interest via transient transfection at plasmid concentration of 50 $\mu g \cdot \mu L^{-1}$ to cells, with an additional gene mix subclone group where all seven genes were transfected to cells at once, but at lower individual plasmid concentration found in the individual case (6.25 $\mu g \cdot \mu L^{-1}$ per gene, total of plasmid concentration of 43.75 $\mu g \cdot \mu L^{-1}$ for seven genes). A negative control was included where no plasmid transfection occurred. Each subclone was cultured for 6 days at which time cells and cell culture supernatant were collected. Cells for both the control and transfection subclones were derived from the same culture to eliminate variation in growth cycle and other culture conditions. Quantification of inhibitory metabolites accumulation was performed through LC-MS. Bars, mean±s.e.m.; n=3, *$p<0.05$, $p<0.01$, *$p<0.001$. Statistics by two-tailed t-test.

FIG. 18A-B are graphs showing the growth profile of different subclones. FIG. 18A shows the viable cell density (VCD) profile. FIG. 18B shows the integral viable cell density (VCD) profile. In this study, each subclone was overexpressed with an individual gene of interest via transient transfection at plasmid concentration of 50 $\mu g \cdot \mu L^{-1}$ to cells, with an additional gene mix subclone where all seven genes were transfected to cells, but at lower concentration (plasmid concentration of 6.25 $\mu g \cdot \mu L^{-1}$ per gene) of the concentration found in the individual case. A negative control was included in the study where no plasmid transfection occurred. Each subclone was cultured for 6 days, of which cell culture supernatant was collected at harvest day.

FIG. 19A shows VCD profile. FIG. 19B shows the integral VCD profile. All seven critical genes were transfected into the host cells to test the overall function and their interactions. Genes mix subclone was overexpressed with all seven genes of interest via transient transfection at plasmid concentration of 6.25 $\mu g \cdot \mu L^{-1}$ per gene. A negative control was included in the study where no plasmid transfection occurred. Each subclone was cultured until cells viability dropped below 80%. Cells for both the control and transfection subclones were derived from the same culture to eliminate variation in growth cycle and other culture conditions.

FIG. 20A, sodium; FIG. 20B, potassium; FIG. 20C, ammonia; FIG. 20D, lactate; FIG. 20E, glucose; FIG. 20F, glutamate; and FIG. 20G, glutamine profile. The study was divided into unique subclone groups. Each subclone was overexpressed with an individual gene of interest via transient transfection at plasmid concentration of 50 $\mu g \cdot \mu L^{-1}$ to cells. A negative control was included in the study where no plasmid transfection occurred. Each subclone was cultured until cells viability dropped below 80%. Cells for both the control and transfection subclones were derived from the same culture to eliminate variation in growth cycle and other culture conditions. More than 50% ammonia decreased was observed, and less glucose consumption in the engineered cell line.

FIG. 21A, Sodium; FIG. 21B, potassium; FIG. 21C, ammonia; FIG. 21D, lactate; FIG. 21E, glucose; FIG. 21F, glutamate, and FIG. 21G, glutamine profile. All seven critical genes were transfected into the host cells to test the overall function and their interactions. Genes mix subclone was overexpressed with all seven genes of interest via transient transfection at plasmid concentration of 6.25 $\mu g \cdot \mu L^{-1}$ per gene. A negative control was included in which no plasmid transfection occurred. Each subclone was cultured until cells viability dropped below 80%. Cells for both the control and transfection subclones were derived from the same culture to eliminate variation in growth cycle and other culture conditions.

Figure 1:
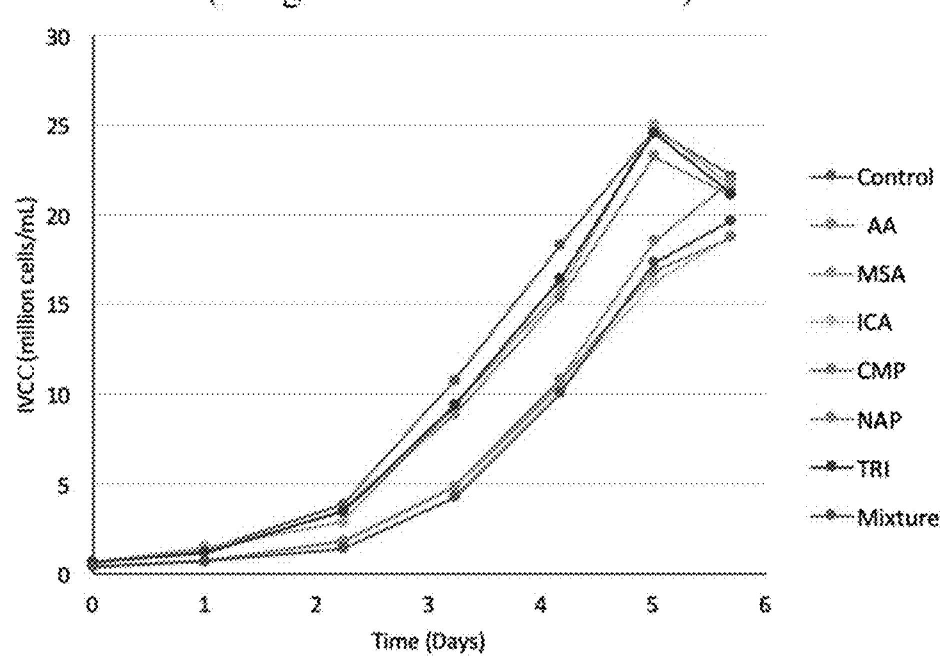
FIG. 1 shows integrated viable cell density as the accumulation of the cells in batch culture. Mixture conditions excluded ICA and included AA, HICA, CMP, MSA, TRI, and NAP.
Figure 2:
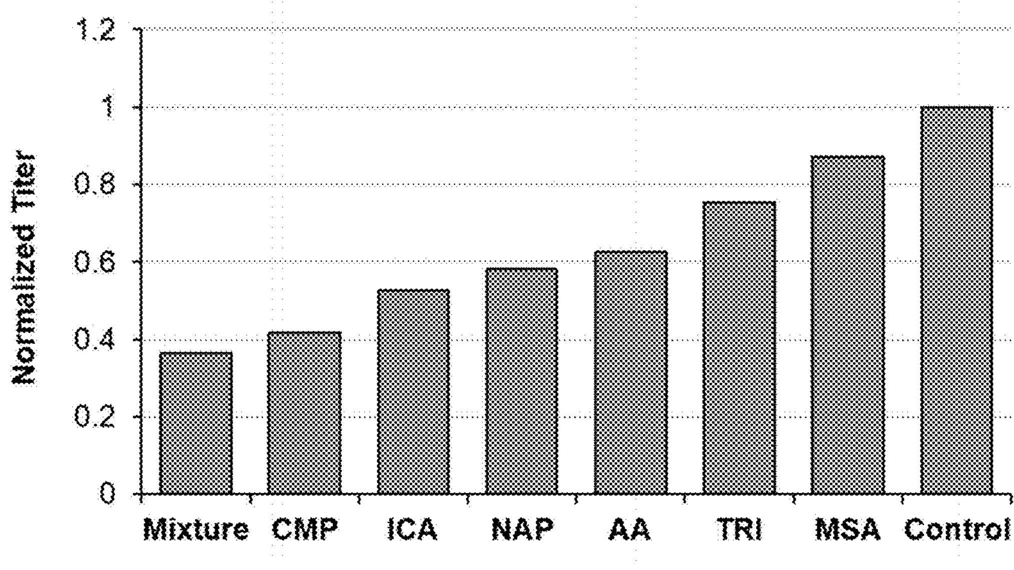
FIG. 2 shows antibody production inhibited by the inhibitory metabolites. Productivity is shown as a normalized scale. Mixture conditions were the same as in FIG. 1.

The above-described and other features will be appreciated and understood by those skilled in the art from the following detailed description, drawings, and appended claims.

DETAILED DESCRIPTION

Chinese hamster ovary (CHO) cells remain as the leading workhorse for monoclonal antibody (mAb) production. To achieve high antibody productivity, the manufacturing process is done in high cell density conditions (>10 million cells/mL). However, the productivity reaches a bottleneck due to large concentrations of inhibitory metabolites secreted while the cell density reaches record highs. The accumulation of these inhibitory metabolites compromises cell growth and also poses a risk to overall product quality as accrual of waste byproducts (such as ammonia) has been shown to alter key product attributes of recombinant proteins. Besides the common inhibitors, in this study novel metabolic biomarkers were identified and characterized by metabolomics using LC-MS. The work flow for the waste inhibitor metabolomics were candidate identification, inhibitory impact verification and quantification, and control strategy development.

The novel biomarkers of protein production in CHO cells and other mammalian cells are aconitic acid (AA), or more specifically aconitic acid (AA), leucinic acid (HICA), cytidine monophosphate (CMP), methylsuccinic acid (MSA), trigonelline (TRI) and N-acetylputrescinium (NAP). Guanosine monophosphate (GMP) and indole-3-carboxylic acid (ICA) which had previously been identified were also identified in the studies herein and can be combined with the biomarkers newly described herein.

Described herein are cell culture methods where the concentration of at least one metabolite selected from aconitic acid (AA), leucinic acid (HICA), cytidine monophosphate (CMP), methylsuccinic acid (MSA), trigonelline (TRI) and N-acetylputrescinium (NAP) is maintained at low levels in the cell culture medium. In cell culture, and in particular in high density cell culture, such as for example fed-batch and/or perfusion bioprocessing aiming at producing high amount of a recombinant protein of interest, the growth of cells can be inhibited by the accumulation of metabolites such AA, HICA, CMP, MSA, TRI and/or NAP. The inhibitory effect of these metabolites can be limited by maintaining their concentration in the cell culture medium below levels where they inhibit cell growth, recombinant protein productivity and product quality. Product quality includes, but is not limited to, glycosylation pattern, charge variants, aggregation and fragmentation, all of which can be controlled by the methods described herein.

In an aspect, a cell culture method comprises (i) culturing cells in a cell culture medium to start a cell culture process, and, (ii) maintaining at least one metabolite selected from AA, HICA, CMP, MSA, TRI and NAP below an inhibitory concentration in the cell culture medium for the at least one metabolite. In an aspect, the cells are mammalian cells.

Exemplary CHO cell lines include CHOK1, CHO GS and DG44. Other mammalian cell lines include cell lines used to produce human therapeutic products such as HEK 293 cells, HT-1080 cells, engineered T cells and engineered natural killer cells.

Inhibitory amounts of the metabolites can be in the range of 1 nm to 50 mM, more specifically 100 nM to 10 mM.

When the metabolite is AA, the inhibitory concentration may be lower than 100 μM, 440 μM, 880 μM, 3 mM, 5 mM or 10 mM.

When the metabolite is HICA, the inhibitory concentration may be lower than 10 μM, 23.5 μM, 47 μM, 100 μM, 1 mM, or 3 mM.

When the metabolite is CMP, the inhibitory concentration may be lower than 5 μM, 10 μM, 20 μM, 100 μM, 500 μM, or 1 mM.

When the metabolite is MSA, the inhibitory concentration may be lower than 1 μM, 3.75 μM, 7.5 μM, 100 μM, 1 mM or 3 mM.

When the metabolite is TRI, the inhibitory concentration may be lower than 0.1 μM, 0.35 μM, 0.7 μM, 100 μM, 1 mM or 3 mM.

When the metabolite is NAP, the inhibitory concentration may be lower than 0.1 μM, 0.3 μM, 0.6 μM, 100 μM, 1 mM or 3 mM.

In an aspect, the method comprises measuring the concentration of the at least one metabolite. The concentration of metabolite can be measured by any method known to an analytical specialist.

The concentration of metabolites can be measured once or several times during the cell culture. In aspects, the metabolite concentration is measured continuously, intermittently, every 30 min, every hour, every two hours, twice a day, daily, or every two days. In a preferred aspect, the concentration of metabolite is measured daily.

The concentration may be measured in a method that is not automated and integrated to the cell culture method. For example, a measurement method where a sample is manually taken from the cell culture medium so that a specific concentration can be measured in the sample may be employed. Alternatively, determining the concentration of the metabolites may be automated and integrated to the cell culture method.

Exemplary methods for measuring the concentration of the metabolites include nuclear magnetic resonance (NMR) spectroscopy, Raman spectroscopy, High/Ultra Performance Liquid Chromatography (H/UPLC), Liquid Chromatography Mass Spectrometer (LC-MS), Gas Chromatography Mass Spectrometer (GC-MS) technology, or a combination thereof. In GC-MS, for example, the experiment can be performed with an auto-sampler that draws samples from reactor and transfers them to the equipment in a programmed manner. In data not shown, the identification of AA, RICA, CMP, MSA, TRI and NAP was confirmed using a combination of one or more of the foregoing methods.

In an aspect, when the measured concentration of the one or more metabolites is above a predefined value such as the inhibitory concentration, a control strategy is employed to limit the concentration of the inhibitory metabolite. In control strategy 1, the concentration of a precursor (e.g., amino acids, glucose) of the at least one metabolite in the cell culture medium is decreased by reducing the amount of the precursor provided to the cells. Limiting the precursors of the metabolites will mitigate the accumulation of the inhibitory metabolites. This method can also be referred to as media control. The predefined value is selected so that the decrease of concentration of the precursor prevents the concentration of the one or more metabolites to rise above the inhibitory concentration.

When the metabolite is AA, the precursor is glutamine, glucose, arginine, and/or asparagine.

When the metabolite is HICA, the precursor is leucine and/or isoleucine.

When the metabolite is CMP, the precursor is glutamine, arginine, and/or aspartate.

When the metabolite is MSA, the precursor is lysine, isoleucine, serine, glucose, and/or glutamine.

When the metabolite is TRI, the precursor is aspartate, tryptophan, and/or glutamine.

When the metabolite is NAP, the precursor is arginine, proline, aspartate glutamine, and/or asparagine.

Combinations of the foregoing precursors may also be decreased in the methods.

Decreasing the concentration of the precursors of the inhibitory metabolites can decrease the inhibitor concentration to optimize the process.

The concentration of precursor in the cell culture medium can be decreased by reducing the amount of precursor provided to the cells, for example by reducing the concentration of the precursor in the feed medium, reducing the feed rate, reducing the number or volume of feeds, or a combination thereof. For example, the feed medium can be replaced by a feed medium comprising a lower concentration of precursor.

The concentration of the precursors can be in the range of 0.01 g/L to 2 g/L. More specifically:

When the precursor is arginine, the concentration may be lower than 0.2 g/L, 0.3 g/L, 0.4 g/L, 0.5 g/L, or 0.6 g/L.

When the precursor is asparagine, the concentration may be lower than 0.1 g/L, 0.3 g/L, 0.5 g/L, 0.7 g/L, or 0.9 g/L.

When the precursor is aspartic acid, the concentration may be lower than 0.1 g/L, 0.3 g/L, 0.5 g/L, 0.7 g/L, or 0.9 g/L.

When the precursor is glutamine, the concentration may be lower than 0.1 g/L, 0.6 g/L, 0.9 g/L, 1.2 g/L, or 1.5 g/L.

When the precursor is isoleucine, the concentration may be lower than 0.05 g/L, 0.15 g/L, 0.25 g/L, 0.35 g/L, or 0.45 g/L.

When the precursor is leucine, the concentration may be lower than 0.1 g/L, 0.2 g/L, 0.3 g/L, 0.4 g/L, or 0.5 g/L.

When the precursor is lysine, the concentration may be lower than 0.1 g/L, 0.2 g/L, 0.3 g/L, 0.4 g/L, or 0.5 g/L.

When the precursor is proline, the concentration may be lower than 0.05 g/L, 0.15 g/L, 0.25 g/L, 0.35 g/L, or 0.45 g/L.

When the precursor is serine, the concentration may be lower than 0.05 g/L, 0.15 g/L, 0.25 g/L, 0.35 g/L, or 0.45 g/L.

When the precursor is tryptophan, the concentration may be lower than 0.01 g/L, 0.03 g/L, 0.07 g/L, 0.1 g/L, or 0.15 g/L.

A design of experiments, such as Plackett-Burman Design or Response Surface Methodology (RSM) can be applied to find the optimum precursor concentration from the above concentration range to minimize inhibitory metabolite accumulation.

Decreasing the amount of glucose, for example, can include culturing cells at low glucose concentrations by using alternative carbon sources including but not limited to fructose and galactose, using a cell line that has reduced protein levels of glycolytic enzymes including but not limited to hexose transporter or lactate dehydrogenase, employing a cell line with suppressed cellular protein levels of both lactate dehydrogenase and pyruvate dehydrogenase kinase, or employing a cell line with over-expression of pyruvate carboxylase enzyme, or with the use of inhibitors (small molecule or protein based) for signaling pathways (such as AKT, mTOR, HIF1a) that regulate the activity of energy metabolism pathways (glycolysis, TCA cycle, and redox pathway).

Figure 10:
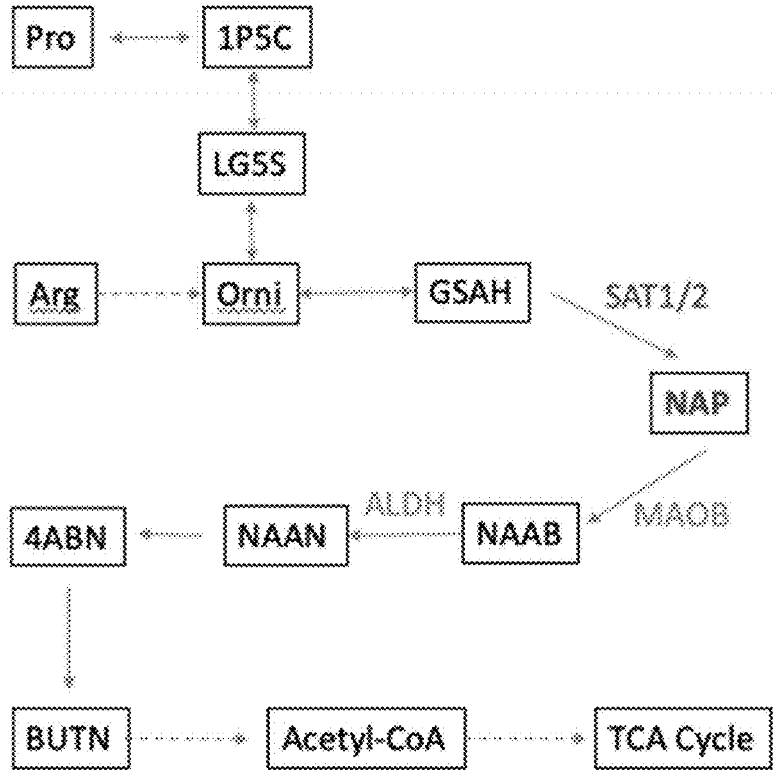
FIG. 10 shows an example of an NAP control strategy. This is the N-acetylputrescinium (NAP) metabolic pathway in CHO cells. Control strategy 1: lower the concentration of proline and arginine in the media, which will lead to reduced production of NAP. In the current CHO cell bioprocessing, overfeeding (too high nutrients) is very common, which will impact the production and quality of the biomanufacturing. Control strategy 2: lower the enzyme (SAT1/2) expression level such as by introducing siRNA. With reduced enzyme expression, the NAP accumulation rate will slow down. In addition, or as an alternative, upregulating the MAOB (monoamine oxidase) expression level to shift the NAP to the downstream TCA cycle, which can provide energy for cell growth and producing protein. Control strategy 3: upregulating the MAOB activity to shift the NAP to downstream TCA cycle, which can provide energy for cell growth and producing protein.
Figure 12:
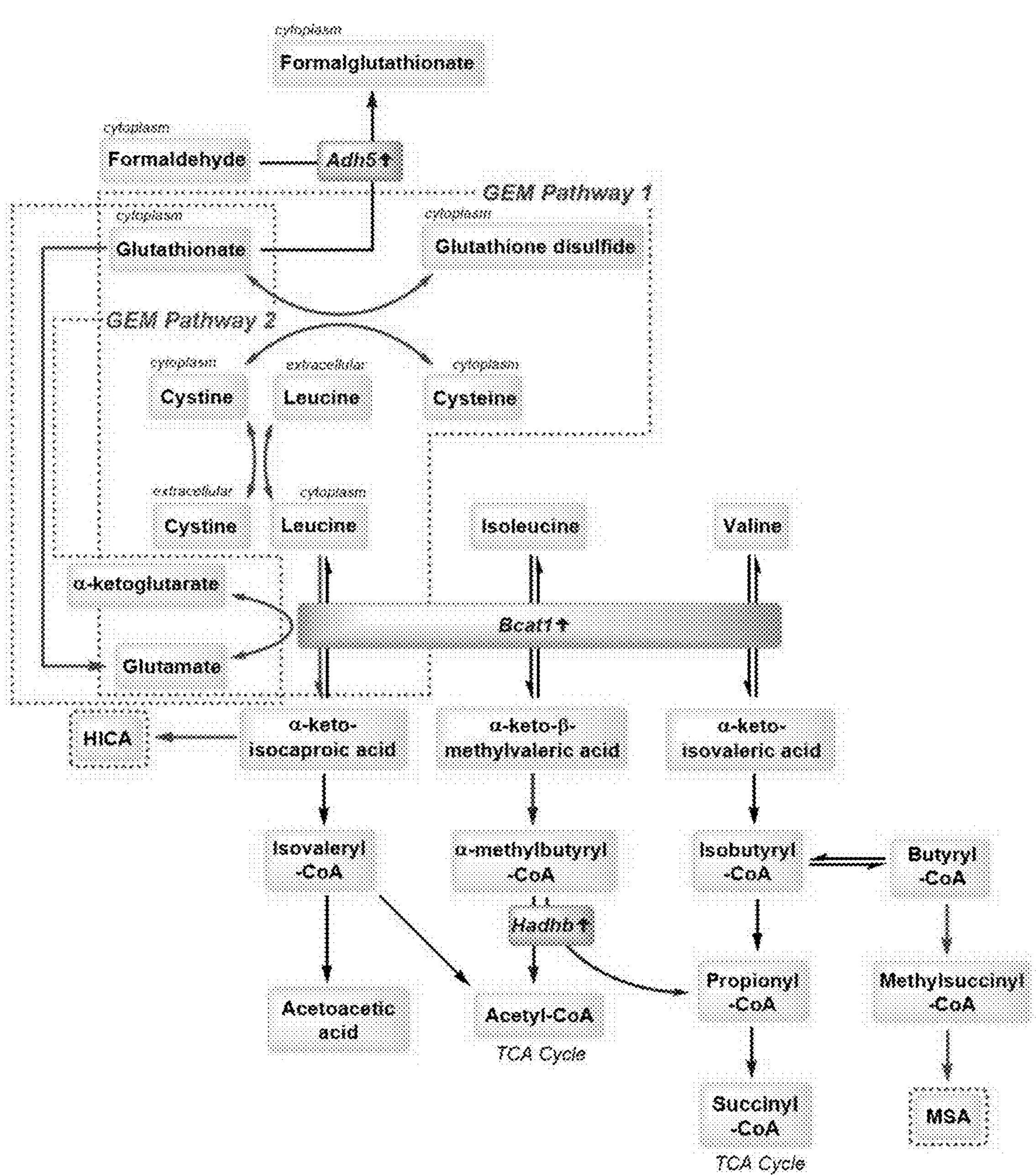
FIG. 12 shows the genetic engineering strategy targeting accumulation of α-hydroxyisocaproic acid (HICA) and methylsuccinic acid (MSA) accumulation in CHO-K1 cells. In this study, metabolic by-products HICA and MSA previously identified to be growth inhibitors accumulated from a batch and fed-batch CHO bioprocess are target for genetic engineering study. Genome scale modeling (GEM) reveals additional metabolic pathways that can be controlled through genetic engineering strategy. Accumulation of inhibitors can be controlled by upregulating the expression of characterized genes (italic) responsible for modulation of metabolic enzymes that catalyze reaction.
Figure 13A:
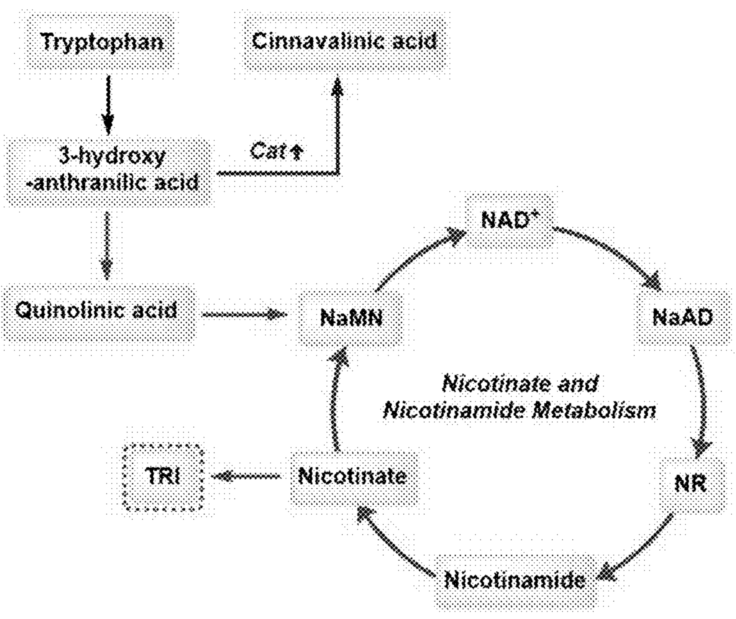
FIG. 13A-D show the genetic engineering strategy targeting accumulation of trigonelline (TRI), N-acetylputrescine (NAP), trans-aconitic acid (TAA) and cytidine-5'-monophosphate (CMP) accumulation in CHO-K1 bioprocess.
Figure 13B:
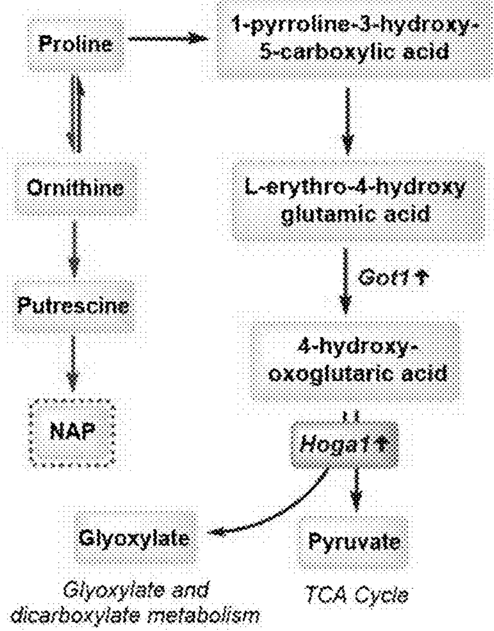
Figure 13C:
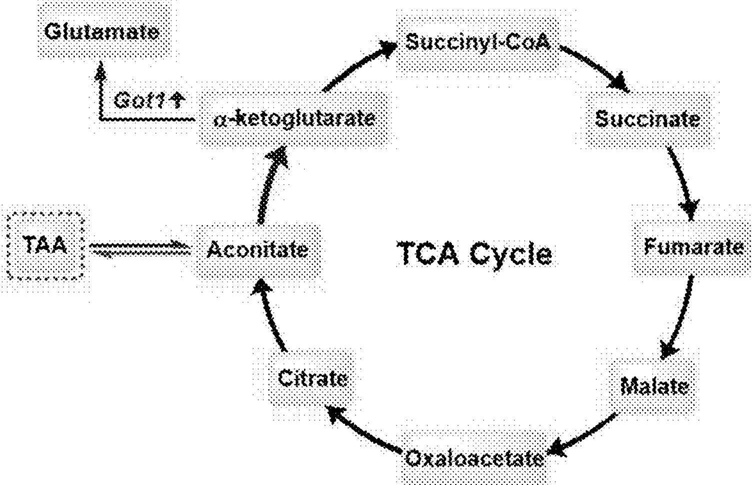
Figure 13D:
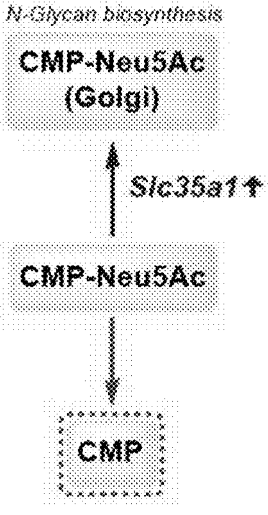

In control strategies 2a and b and 3, the upstream and downstream enzyme expression (strategy 2) or activity (strategy 3) is manipulated to mitigate the synthesis of the inhibitory metabolites. The general idea behind control strategies 2 and 3 is to down regulate the upstream enzyme so that the cells will produce less inhibitory metabolites and/or to upregulate the downstream enzymes so that the cells will consume the metabolites to generate energy. FIG. 10 shows three control strategies illustrated for NAP, FIG. 12 shows control strategies for MSA and HICA, FIG. 13A shows control strategy for TRI, FIG. 13B shows an additional control strategy for NAP, FIG. 13C shows a control strategy for TAA, and FIG. 13D shows a control strategy for CMP.

In control strategy 2a, the upstream and/or downstream enzyme expression which controls the level of the metabolite may be regulated using an inhibitory nucleic acid, such as an siRNA. The term "inhibitory nucleic acid" means a single stranded or double-stranded RNA or DNA, specifically RNA, such as triplex oligonucleotides, ribozymes, aptamers, small interfering RNA including siRNA (short interfering RNA) and shRNA (short hairpin RNA), antisense RNA, or a portion thereof, or an analog or mimetic thereof, that is capable of reducing or inhibiting the expression of a target gene or sequence. Inhibitory nucleic acids can act by, for example, mediating the degradation or inhibiting the translation of mRNAs which are complementary to the interfering RNA sequence. An inhibitory nucleic acid, when administered to a mammalian cell, results in a decrease (e.g., by 5%, 10%, 25%, 50%, 75%, or even 90-100%) in the expression (e.g., transcription or translation) of a target sequence. Typically, a nucleic acid inhibitor comprises or corresponds to at least a portion of a target nucleic acid molecule, or an ortholog thereof, or comprises at least a portion of the complementary strand of a target nucleic acid molecule. Inhibitory nucleic acids may have substantial or complete identity to the target gene or sequence, or may include a region of mismatch (i.e., a mismatch motif). The sequence of the inhibitory nucleic acid can correspond to the full-length target gene, or a subsequence thereof. In one aspect, the inhibitory nucleic acid molecules are chemically synthesized.

In control strategy 2b, recombinant DNA is used to overexpress one or more downstream enzymes which controls the level of the metabolite, thus reducing the level of the metabolite.

In control strategy 3, enzyme activation can be controlled by two different approaches:

Approach 1: regulating enzyme expression to reduce the synthesis of the metabolite comprises adding an inhibitor of enzyme activity. Exemplary inhibitors of enzyme activity include small molecules, peptides, proteins and nucleic acids that bind the active site of the enzyme and interfere with the activity of the enzyme.

Approach 2: As all the inhibitory metabolites can be further metabolized to the TCA cycle to provide energy, glycolytic pathway activators, such as HK-1 and GK, can be used to mitigate the accumulation of inhibitory metabolites.

For control strategies 2 and 3 in certain aspects wherein the metabolite is AA and the enzyme is ADI1, HOGA1, TAD1, or a combination thereof;

wherein the metabolite is HICA and the enzyme is ADH5, BCAT1, SLC35A1, GOT1, D-HicDH, MMUT, AUH, HMGCL, HADHA/B, or a combination thereof;

wherein the metabolite is CMP and the enzyme is UCK1/2, NTS, CMAS, CMPK1, DDYD, CDA, SLC35A1, RRM1, HOGA1, CAT, ADH5, BCAT1, GOT1, HADHA/B, or a combination thereof;

wherein the metabolite is MSA and the enzyme is BCAT1, GOT1, ETHE1, AMT, HADHA/B, MMUT, HOGA1, SLC35A1, or a combination thereof;

wherein the metabolite is TRI and the enzyme is BCAT1, GOT1, HADHA/B, NADSYN1, NNMT, CAT, HOGA1, SLC35A1, NMNAT1, SULT4A1, or a combination thereof;

wherein the metabolite is NAP and the enzyme is BCAT1, SLC35A1, CAT, HADHA/B, SAT1/2, HOGA1, AMD1, ODC1, GOT1, MAOB, or a combination thereof;

wherein the metabolite is TAA and the enzyme is BCAT1, ADH5, GOT1, HOGA1, SLC35A1, HADHB, or a combination thereof; or a combination thereof.

In an aspect, the enzyme comprises ADH5, BCAT1, CAT, GOT1, HADHB, HOGA1, SLC35A1, or a combination thereof. In certain aspects, wherein the metabolite is HICA and the enzyme comprises ADH5, BCAT1, SLC35A1, GOT1, HADHB, or a combination thereof;

wherein the metabolite is CMP and the enzyme comprises ADH5, BCAT1, CAT, GOT1, HOGA1, SLC35A1, HADHB or a combination thereof;

wherein the metabolite is MSA and the enzyme comprises BCAT1, GOT1, HADHB, HOGA1, SLC35A1 or a combination thereof or a combination thereof;

wherein the metabolite is TRI and the enzyme comprises BCAT1, GOT1, HADHB, CAT, HOGA1, SLC35A1, or a combination thereof;

wherein the metabolite is NAP and the enzyme comprises BCAT1, SLC35A1, HOGA1, GOT1, CAT, HADHB or a combination thereof;

wherein the metabolite is TAA and the enzyme is BCAT1, ADH5, GOT1, HOGA1, SLC35A1, HADHB, or a combination thereof; or a combination thereof.

In an aspect, the enzyme comprises ADH5, BCAT1, GOT1, HADHA/B, HOGA1, SLC35A1, and CAT.

In control strategy 4, maintaining the at least one metabolite below an inhibitory concentration in the cell culture medium for the at least one metabolite comprises controlling process parameters, including temperature, dissolved oxygen level, pH, or a combination thereof. The optimal temperature, dissolved oxygen level and pH can be determined by the rate of the enzymatic reaction and inhibitory metabolites accumulation. The process may be optimized for fed-batch and perfusion bioprocesses.

Exemplary temperatures are about 30° C. to about 40° C., specifically, temperatures of 31° C., 32° C., 33° C., 34° C., 35° C., 36° C. and 37° C. in the early phase and late phase of cell culture.

Exemplary pHs are in the range of pH 5.5 to 8.5, such as pH 6.5, 6.7, 6.9, 7, 7.2, 7.4, or 7.6. $CO_2$ sparging and/or $Na_2CO_3$ supplementation can be used to balance the pH. Exemplary $CO_2$ sparging rates include 0.3 SLPH, 0.4 SLPH, 0.5 SLPH, 0.6 SLPH and 0.7 SLPH (standard liter per hour). Exemplary agitation rates for $Na_2CO_3$ supplementation include 90 RPM, 120 RPM, 150 RPM and 170 RPM (rounds per minute).

Exemplary dissolved oxygen set points include 5% to 50%, such as 20%, 30% and 40%.

Any cell which can be grown in cell culture can be used in the methods described herein. In some aspects, the cell is a mammalian cell. Non-limiting examples of mammalian cells include BALB/c mouse myeloma lines (NSO/I, ECACC No: 85110503); human retinoblasts (PER.C6, CruCell, Leiden, The Netherlands); monkey kidney CV1 lines transformed by SV40 (COS-7, ATCC CRL 1651); human embryonic kidney lines (293 or 293 cells subcloned for growth in suspension); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In an aspect, the cells are CHO cells, HEK 293 cells, HT-1080 cells, engineered T cells and engineered natural killer cells. Engineered T-cells include CAR T cells.

Any number of commercially and non-commercially available hybridoma cell lines may be utilized in the methods described herein. The term “hybridoma” as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, goat, and human. In some aspects, a hybridoma is a trioma cell line, which results when progeny of heterohybrid myeloma fusions, which are the product of a fusion between human cells and a murine myeloma cell line, are subsequently fused with a plasma cell. In some aspects, a hybridoma is any immortalized hybrid cell line that produces antibodies such as, for example, quadromas. One skilled in the art will appreciate that hybridoma cell lines might have different nutrition requirements and/or might require different culture conditions for optimal growth, and will be able to modify conditions as needed.

The terms “culture” and “cell culture” as used herein refer to a cell population that is suspended in a medium under conditions suitable to survival and/or growth of the cell population. As will be clear to those of ordinary skill in the art, in some aspects, these terms as used herein refer to the combination comprising the cell population and the medium in which the population is suspended. In some aspects, the cells of the cell culture comprise mammalian cells.

The methods described herein may be used with any cell culture method that is amenable to the desired process (e.g., production of a recombinant protein (e.g., antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the methods described herein.

In some aspects, a cell culture is a fed-batch culture. The term “fed-batch culture” as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some aspects, the fed-batch culture comprises a base medium supplemented with feed media.

Alternatively, the cells may be grown in a perfusion process. In a perfusion process, cells are retained in the bioreactor while continually removing cell waste products and depleted media. Fresh media is added at roughly the same rate as depleted media is removed from the system. Removing spent media can be done by alternating tangential flow, standard tangential flow filtration, hollow fiber filtration, and the like.

Cells may be grown in any convenient volume chosen by the practitioner. For example, cells may be grown in small scale reaction vessels ranging in volume from a few milliliters to several liters. Alternatively, cells may be grown in large scale commercial bioreactors ranging in volume from approximately at least 1 liter to 10, 50, 100, 250, 500, 1000, 2500, 5000, 8000, 10,000, 12,000, 15000, 20000 or 25000 liters or more, or any volume in between.

The temperature of a cell culture will be selected based primarily on the range of temperatures at which the cell culture remains viable and the range in which a high level of desired product (e.g., a recombinant protein) is produced. In general, most mammalian cells grow well and can produce desired products (e.g., recombinant proteins) within a range of about 25° C. to 42° C., although the methods described herein are not limited to these temperatures. Certain mammalian cells grow well and can produce desired products (e.g., recombinant proteins or antibodies) within the range of about 35° C. to 40° C. In certain aspects, a cell culture is grown at a temperature of 20-45° C. at one or more times during the cell culture process. Those of ordinary skill in the art will be able to select appropriate temperature or temperatures in which to grow cells, depending on the particular needs of the cells and the particular production requirements of the practitioner. The cells may be grown for any amount of time, depending on the needs of the practitioner and the requirement of the cells themselves. In an aspect, the cells are grown at 37° C. In other aspects, the cells are grown at 36.5° C.

In some aspects, the cells are grown during the initial growth phase (or growth phase) for a greater or lesser amount of time, depending on the needs of the practitioner and the requirement of the cells themselves. In some aspects, the cells are grown for a period of time sufficient to achieve a predefined cell density. In some aspects, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1-99 percent of maximal cell density. In some aspects, the cells are grown until the cell density does not increase by more than 15%, 14%, 13%, 12%, 11%, 10%, 9%, 8%, 7%, 6%, 5%, 4%, 3%, 2% or 1% per day of culture. In some aspects, the cells are grown until the cell density does not increase by more than 5% per day of culture.

In some aspects, the cells are allowed to grow for a defined period of time. For example, depending on the starting concentration of the cell culture, the temperature at which the cells are grown, and the intrinsic growth rate of the cells, the cells may be grown for 0-20 or more days, specifically for 4 to 10 days. In some cases, the cells may be allowed to grow for a month or more. The practitioner will be able to choose the duration of the initial growth phase depending on protein production requirements and the needs of the cells themselves.

The cell culture may be agitated or shaken during the initial culture phase in order to increase oxygenation and dispersion of nutrients to the cells. One of ordinary skill in the art will understand that it can be beneficial to control or regulate certain internal conditions of the bioreactor during the initial growth phase, including but not limited to pH, temperature, oxygenation, and the like.

At the end of the initial growth phase, at least one of the culture conditions may be shifted so that a second set of culture conditions is applied and a metabolic shift occurs in the culture. A metabolic shift can be accomplished by, e.g., a change in the temperature, dissolved oxygen level, pH, osmolality or chemical inductant level of the cell culture. In one non-limiting aspect, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, dissolved oxygen, osmolality, and sodium butyrate levels. The timing of the culture shift will be determined by the practitioner, based on protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

In some aspects, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, dissolved oxygen, pH, osmolality, and sodium butyrate levels. In some aspects, the temperature of the culture is shifted. According to this aspect, during the subsequent production phase, the culture is maintained at a temperature or temperature range that is lower than the temperature or temperature range of the initial growth phase. As discussed above, multiple discrete temperature shifts may be employed to increase cell density or viability or to increase expression of the recombinant protein.

The cells can express a recombinant protein, a gene product, or a cell product. In some aspects, the cells express a recombinant protein and the cell culture method comprises a growth phase and a production phase. The method described herein may be applied during the growth phase, the production phase, or both.

The methods described herein can be used for improving cell growth in high density cell culture at high cell density. High cell density as used herein refers to cell density above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, preferably above $1\times10^7$ cells/mL, more preferably above $5\times10^7$ cells/mL.

In some aspects, cell growth is determined by viable cell density (VCD), maximum viable cell density, or integrated viable cell count (IVCC; also referred to as integrated viable cell density). In some aspects, cell growth is determined by maximum viable cell density. The term "viable cell density" as used herein refers to the number of cells present in a given volume of medium. Viable cell density can be measured by any method known to the skilled person. Preferably, viable cell density is measured using an automated cell counter such as Bioprofile Flex®. The term maximum cell density as used herein refers to the maximum cell density achieved during the cell culture. The term "cell viability" as used herein refers to the ability of cells in culture to survive under a given set of culture conditions or experimental variations. For example, one may use a dye (e.g., trypan blue) that does not pass through the membrane of a living cell, but can pass through the disrupted membrane of a dead or dying cell in order to determine cell viability.

The terms "Integrated viable cell count (IVCC)" or "integrated viable cell density (IVCD)" as used herein refer to as the area under the viable cell density (VCD) curve. IVCC can be calculated using the following formula:

$$IVCC_{t+1} = IVCC_t + (VCD_t + VCD_{t+1}) * (\Delta t)/2$$

where Δt is the time difference between t and t+1 time points. $IVCC_{t=0}$ can be assumed negligible. $VCD_t$ and $VCD_{t+1}$ are viable cell densities at t and t+1 time points.

The term "titer" as used herein refers, for example, to the total amount of recombinantly expressed protein produced by a cell culture in a given amount of medium volume. Titer is typically expressed in units of grams of protein per liter of medium.

In some aspects, cell growth is increased by at least 5%, 10%, 15%, 20% or 25% as compared to a control culture. A control culture can be identical to the culture described above except it is not cultured using step (ii). In some aspects, cell growth is increased by at least 10% as compared to a control culture. In some aspects, cell growth is increased by at least 20% as compared to a control culture.

In some aspects, the productivity is determined by titer and/or volumetric productivity. The term "titer" as used herein refers, for example, to the total amount of recombinantly expressed protein produced by a cell culture in a given amount of medium volume. Titer is typically expressed in units of grams of protein per liter of medium. In some embodiments, the productivity is determined by titer. In some aspects, the productivity is increased by at least 5%, 10%, 15%, 20% or 25% as compared to the control culture. In some aspects, the productivity is increased by at least 10% as compared to a control culture. In some aspects, the productivity is increased by at least 20% as compared to a control culture.

In some aspects, the maximum cell density of the cell culture is greater than $1\times10^6$ cells/mL, $5\times10^6$ cells/mL, $1\times10^7$ cells/mL, $5\times10^7$ cells/mL, $1\times10^8$ cells/mL or $5\times10^8$ cells/mL. In some aspects, the maximum cell density of the cell culture is greater than $5\times10^6$ cells/mL. In some aspects, the maximum cell density of the cell culture is greater than $1\times10^8$ cells/mL.

The terms "medium", "cell culture medium" and "culture medium" as used herein refer to a solution containing nutrients which nourish growing mammalian cells. Typically, such solutions provide essential and non-essential amino acids, vitamins, energy sources, lipids, and trace elements required by the cell for minimal growth and/or survival. Such a solution may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some aspects, a medium is advantageously formulated to a pH and salt concentration optimal for cell survival and proliferation. In some aspects, a medium is a feed medium that is added after the beginning of the cell culture.

A wide variety of mammalian growth media may be used in accordance with the methods described herein. In some aspects, cells may be grown in one of a variety of chemically defined media, wherein the components of the media are both known and controlled. In some aspects, cells may be grown in a complex medium, in which not all components of the medium are known and/or controlled.

Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media generally comprise high amounts of nutrients and in particular of amino acids to support the growth and/or the maintenance of cells at high density. If necessary, these media can be modified by the skilled person for use in the methods described herein.

Not all components of complex media are well characterized, and so complex media may contain additives such as simple and/or complex carbon sources, simple and/or complex nitrogen sources, and serum, among other things. In some aspects, complex media contains additives such as hydrolysates in addition to other components of defined medium as described herein.

In some aspects, defined media typically includes roughly fifty chemical entities at known concentrations in water. Most of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some aspects, supplementary components may be added to the initial cell culture. In some aspects, supplementary components may be added after the beginning of the cell culture.

Typically, trace elements refer to a variety of inorganic salts included at micromolar or lower levels. For example, commonly included trace elements are zinc, selenium, copper, and others. In some aspects, iron (ferrous or ferric salts) can be included as a trace element in the initial cell culture medium at micromolar concentrations. Manganese is also frequently included among the trace elements as a divalent cation ($MnCl_2$ or $MnSO_4$) in a range of nanomolar to micromolar concentrations. Numerous less common trace elements are usually added at nanomolar concentrations.

In some aspects, the medium used in the method is a medium suitable for supporting high cell density, such as for example $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, in a cell culture. In some aspects, the cell culture is a mammalian cell fed-batch culture, preferably a CHO cells fed-batch culture.

In many instances, the cells will be selected or engineered to produce high levels of desired products (e.g., recombinant protein or antibody). Often, cells will be manipulated to produce high levels of recombinant protein, for example by introduction of a gene encoding the protein of interest and/or by introduction of genetic control elements that regulate expression of that gene (whether endogenous or introduced).

Certain proteins may have detrimental effects on cell growth, cell viability or some other characteristic of the cells that ultimately limits production of the protein of interest in some way. Even amongst a population of cells of one particular type engineered to express a specific protein, variability within the cellular population exists such that certain individual cells will grow better, produce more protein of interest, or produce a protein with higher activity levels (e.g., enzymatic activity). In certain aspects, a cell line is empirically selected by the practitioner for robust growth under the particular conditions chosen for culturing the cells. In some aspects, individual cells engineered to express a particular protein are chosen for large-scale production based on cell growth, final cell density, percent cell viability, titer of the expressed protein or any combination of these or any other conditions deemed important by the practitioner.

Any protein that is expressible in a host cell may be produced in accordance with the methods described herein. The term "host cell" as used herein refers to a cell that is manipulated to produce a protein of interest as described herein. A protein may be expressed from a gene that is endogenous to the cell, or from a heterologous gene that is introduced into the cell. A protein may be one that occurs in nature, or may alternatively have a sequence that was engineered or selected.

Proteins that may desirably be expressed will often be selected on the basis of an interesting or useful biological or chemical activity. For example, the methods may be employed to express any pharmaceutically or commercially relevant enzyme, receptor, antibody, hormone, regulatory factor, antigen, binding agent, etc. In some aspects, the protein expressed by cells in culture are selected from antibodies, or fragments thereof, nanobodies, single domain antibodies, glycoproteins, therapeutic proteins, growth factors, clotting factors, cytokines, fusion proteins, pharmaceutical drug substances, vaccines, enzymes, or Small Modular ImmunoPharmaceuticals™ (SMIPs). One of ordinary skill in the art will understand that any protein that may be expressed and will be able to select the particular protein to be produced based on his or her particular needs.

Production of antibodies is of particular interest in accordance with the present methods. Antibodies are proteins that have the ability to specifically bind a particular antigen. Any antibody that can be expressed in a host cell may be produced. In some aspects, the antibody to be expressed is a monoclonal antibody.

In some aspects, the monoclonal antibody is a chimeric antibody. A chimeric antibody contains amino acid fragments that are derived from more than one organism. Chimeric antibody molecules can include, for example, an antigen binding domain from an antibody of a mouse, rat, or other species, with human constant regions.

In some aspects, the monoclonal antibody is a human antibody derived, e.g., through the use of ribosome-display or phage-display libraries or the use of xenographic species in which the native antibody genes are inactivated and functionally replaced with human antibody genes, while leaving intact the other components of the native immune system.

In some aspects, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the complementarity determining regions are replaced, at least in part, with residues from a non-human species that confer a desired antigen specificity or affinity. Such altered immunoglobulin molecules can be made by any of several techniques known in the art.

In some aspects, the monoclonal, chimeric, or humanized antibodies described above may contain amino acid residues that do not naturally occur in any antibody in any species in nature. These foreign residues can be utilized, for example, to confer novel or modified specificity, affinity or effector function on the monoclonal, chimeric or humanized antibody. In some aspects, the antibodies described above may be conjugated to drugs for systemic pharmacotherapy, such as toxins, low-molecular-weight cytotoxic drugs, biological response modifiers, and radionuclides.

Generally, a nucleic acid molecule introduced into the cell encodes the protein desired to be expressed. Alternatively, a nucleic acid molecule may encode a gene product that induces the expression of the desired protein by the cell. For example, introduced genetic material may encode a transcription factor that activates transcription of an endogenous or heterologous protein. Alternatively or additionally, an introduced nucleic acid molecule may increase the translation or stability of a protein expressed by the cell. Methods suitable for introducing nucleic acids sufficient to achieve expression of a protein of interest into mammalian host cells are known in the art. For mammalian cells, common methods of introducing genetic material into mammalian cells include the calcium phosphate precipitation method or the Lipofectamine™ method.

In some aspects, a nucleic acid to be introduced is in the form of a naked nucleic acid molecule. For example, the nucleic acid molecule introduced into a cell may consist only of the nucleic acid encoding the protein and the necessary genetic control elements. Alternatively, a nucleic acid encoding the protein (including the necessary regulatory elements) may be contained within a plasmid vector. Non-limiting representative examples of suitable vectors for expression of proteins in mammalian cells include pCDNA1; pCD; pMCIneo Poly-A; a baculovirus vector such as pAC 373 or pAC 610; CDM8; and pMT2PC. In some aspects, a nucleic acid molecule to be introduced into a cell is contained within a viral vector. For example, a nucleic acid encoding the protein may be inserted into the viral genome (or a partial viral genome). Regulatory elements directing the expression of the protein may be included with the nucleic acid inserted into the viral genome (i.e., linked to the gene inserted into the viral genome) or can be provided by the viral genome itself Naked DNA can be introduced into cells by forming a precipitate containing the DNA and calcium phosphate.

Alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (e.g., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection. Alternatively, naked DNA can also be introduced into cells by complexing the DNA to a cation, such as polylysine, which is coupled to a ligand for a cell-surface receptor. Binding of the DNA-ligand complex to the receptor facilitates uptake of the DNA by receptor-mediated endocytosis.

Defective retroviruses are well characterized for use in gene transfer for gene therapy purposes. A recombinant retrovirus can be constructed having a nucleic acid encoding a protein of interest inserted into the retroviral genome. Additionally, portions of the retroviral genome can be removed to render the retrovirus replication defective. Such a replication defective retrovirus is then packaged into virions which can be used to infect a target cell through the use of a helper virus by standard techniques. For example, the genome of an adenovirus can be manipulated such that it encodes and expresses a protein of interest but is inactivated in terms of its ability to replicate in a normal lytic viral life cycle. Exemplary adenoviral vectors derived from the adenovirus strain Ad type 5 d1324 or other strains of adenovirus (e.g., Ad2, Ad3, Ad7 etc.) are known to those skilled in the art. Adeno-associated virus (AAV) is a naturally occurring defective virus that requires another virus, such as an adenovirus or a herpes virus, as a helper virus for efficient replication and a productive life cycle.

When the method used to introduce nucleic acid molecules into a population of cells results in modification of a large proportion of the cells and efficient expression of the protein by the cells, the modified population of cells may be used without further isolation or subcloning of individual cells within the population. That is, there may be sufficient production of the protein by the population of cells such that no further cell isolation is needed and the population can be immediately used to seed a cell culture for the production of the protein. Alternatively, it may be desirable to isolate and expand a homogenous population of cells from a few cells or a single cell that efficiently produce(s) the protein.

Alternative to introducing a nucleic acid molecule into a cell that encodes a protein of interest, the introduced nucleic acid may encode another polypeptide or protein that induces or increases the level of expression of the protein produced endogenously by a cell. For example, a cell may be capable of expressing a particular protein but may fail to do so without additional treatment of the cell. Similarly, the cell may express insufficient amounts of the protein for the desired purpose. Thus, an agent that stimulates expression of the protein of interest can be used to induce or increase expression of that protein by the cell. For example, the introduced nucleic acid molecule may encode a transcription factor that activates or upregulates transcription of the protein of interest. Expression of such a transcription factor in turn leads to expression, or more robust expression of the protein of interest.

In general, it will typically be desirable to isolate and/or purify recombinant proteins, gene products, or cell products expressed according to the methods described herein. In certain aspects, the expressed protein is secreted into the medium and thus cells and other solids may be removed, as by centrifugation or filtering for example, as a first step in the purification process.

Alternatively, the expressed protein may be bound to the surface of the host cell. For example, the media may be removed and the host cells expressing the protein are lysed as a first step in the purification process. Lysis of mammalian host cells can be achieved by any number of means well known to those of ordinary skill in the art, including physical disruption by glass beads and exposure to high pH conditions.

The expressed protein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of protein.

In certain aspects, produced polypeptides or proteins will have pharmacologic activity and will be useful in the preparation of pharmaceuticals. Proteins and peptides may be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. Pharmaceutical compositions typically include a purified polypeptide or protein expressed from a mammalian cell line, a delivery agent in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

The invention is further illustrated by the following non-limiting examples.

EXAMPLES

Example 1

Inhibitor Identification

HILIC liquid chromatography column Orbitrap™ mass spectroscopy (LC-MS) was used to screen the whole CHO metabolome. 30,000 features were analyzed, and more than 1000 features were accumulated throughout the cell culture. The inhibitory impact of the top 20 features were tested analytically and biologically. Table 1 provides the metabolites structurally confirmed by (LC-MS). The end of culture concentration was measured also using the LC-MS with a different method.

TABLE 1

Structurally confirmed metabolites with their end of culture supernatant concentration.

| | Verified Metabolites | MS2 | Exp | m/z | RT | Confirmed |
|---|---|---|---|---|---|---|
| 6 | Indole-3-carboxylic acid (ICA) | 0.9300 | Neg | 160.0393 | 2.2 | 2.5 |
| 8 | Methylsuccinic acid (MSA) | 0.8900 | | 131.0339 | 3.11 | 13.59 |
| 10 | Aconitic acid (AA) | 0.7100 | Neg | 173.0081 | 4.55 | 14359 |
| 25 | Leucinic acid (HICA) | 0.62 | Neg | 131.0703 | 2.26 | 64.09 |
| 1 | Trigonelline (TRI) | 0.6800 | Pos | 138.0550 | 12.9 | 0.812 |
| 3 | N-Acetylputrescinium (NAP) | 0.9400 | Pos | 131.1179 | 15.34 | 0.196 |
| 4 | Cytidine monophosphate (CMP) | 1; 0.87 | Pos (Neg) | 324.0591;322.0435 | 18.45 | 11.27 |
| 5 | Guanosine monophosphate (GMP) | 0.99; 0.87 | Pos (Neg) | 364.0653;362.0496 | 18.29 | 20 |

Example 2

Standard Bioprocesses and Biological Confirmation of Metabolites

CHO K-1 industrial standard batch process: NIH CHO-K1 cell line is cultured for 6 days, with 6 mM glutamine supplement on the inoculation day. The working volume is 30 mL in 125 mL shake flasks, and the inoculation cell density is 0.5 million cells/mL. The parameters for the shaking incubator are: 125 RPM, and 5% $CO_2$.

CHO GS industrial standard batch process: CHOZn® cell line is cultured for 6 days. The working volume is 30 mL in 125 mL shake flasks, and the inoculation cell density is 0.5 million cells/mL. The parameters for the shaking incubator are: 125 RPM, and 5% $CO_2$.

HEK 293 industrial standard batch process: MBL HEK 293 cell line is cultured for 6 days. The working volume is 30 mL in 125 mL shake flasks, and the inoculation cell density is 0.5 million cells/mL, with 6 mM glutamine supplement on the inoculation day. The parameters for the shaking incubator are: 125 RPM, and 5% $CO_2$.

Figure 3:
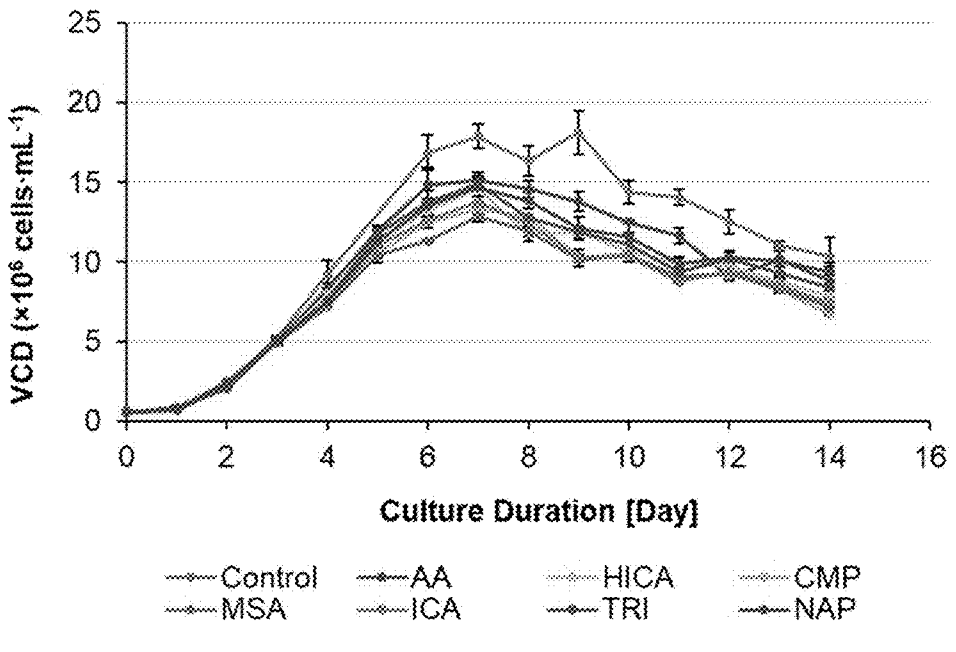
FIG. 3 shows a viable cell density plot for a fed-batch spiking test.
Figure 4:
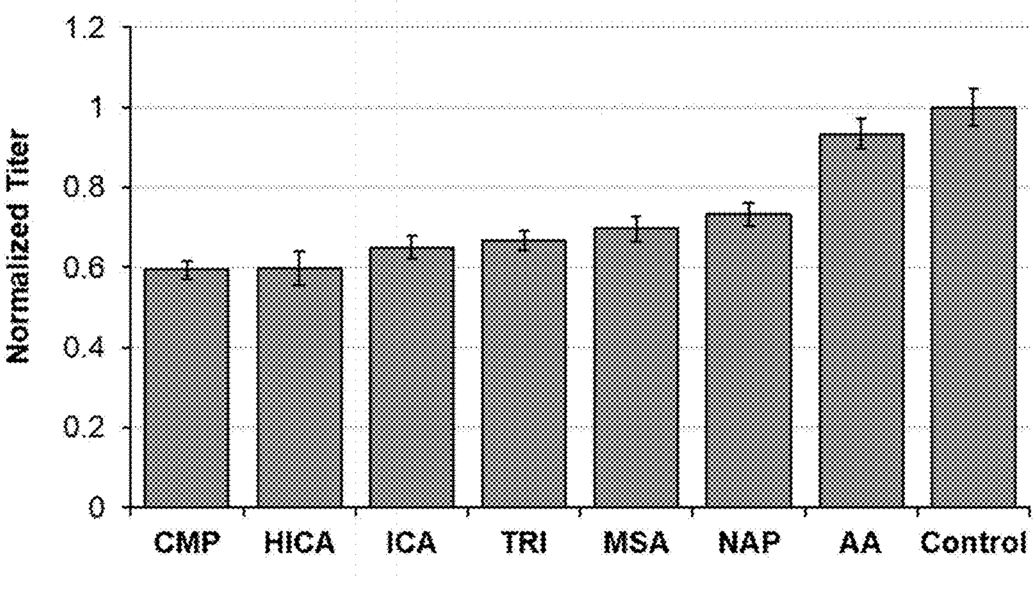
FIG. 4 shows that HICA, CMP, ICA and TRI (30-40% titer drop compared to the control) showed stronger productivity inhibition. The values are harvest (Day 14) titer values, measured by HPLC with triplicate standard curves.

Cells were exposed to the identified inhibitory metabolites of Table 1 at their end-of-culture concentration for 6 days in batch culture. AA, ICA, CMP, and mixture condition showed lower cell density than the control group (FIG. 3). All of the inhibitory metabolites decreased the antibody productivity (FIG. 4).

Industrial standard Fed-batch process: CHO-K1 cell line is cultured in corresponding media. Feed for 14 days, with 6 mM glutamine supplement on the inoculation day. The working volume is 30 mL in 125 mL shake flasks, and the inoculation cell density is 0.5 million cells/mL. The parameters for the shaking incubator are: 125 RPM, and 5% $CO_2$. The feeding strategy is 10% corresponding feed everyday starting from day 3 to day 13.

In the standard industrial fed-batch process, cells were exposed to the inhibitors for a long period of time. This experiment mimics the therapeutic antibody production process, and spikes the inhibitors at their end-of-culture cellular concentration. ICA was confirmed as a known inhibitor and was used as a positive inhibitor control. Mixture condition excluded ICA and included AA, HICA, CMP, MSA, TRI, NAP. The process lasted for 14 days, and starting from day 6, the cell density under the inhibitor conditions were lower than the negative control batch. The results are shown in FIG. 3. Comparing to the control batch, CMP, ICA, TRI and HICA showed stronger growth inhibition impact, leading to a 40-50% VCD drop at the peak VCD on Day 9.

Example 3

Shows Productivity and Quality Impact of the Metabolites

IgG titer was measured by HPLC with a Protein A column. Product quality was quantified by the IgG glycan profile, which was measured by HPLC with a Glycan Column.

Figure 5:
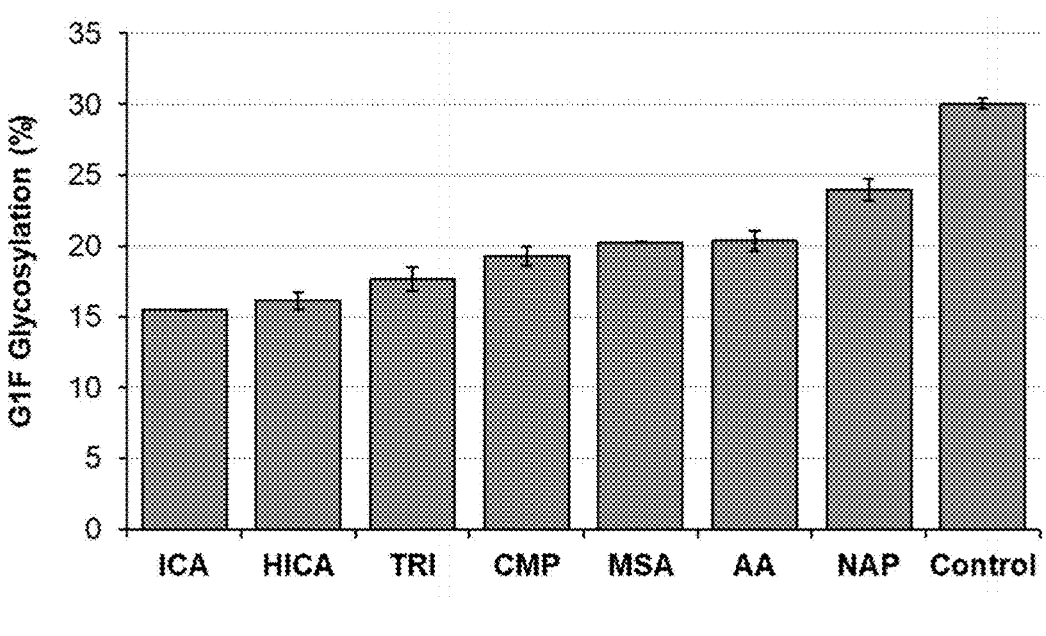
FIG. 5 shows the product quality impact on G1F, one of the glycan profile species found on IgG antibody drugs, indicating the glycosylation level. Compared to control group (column 9), AA, HICA, CMP, MSA, and ICA had a higher impact on G1F formation.
Figure 6:
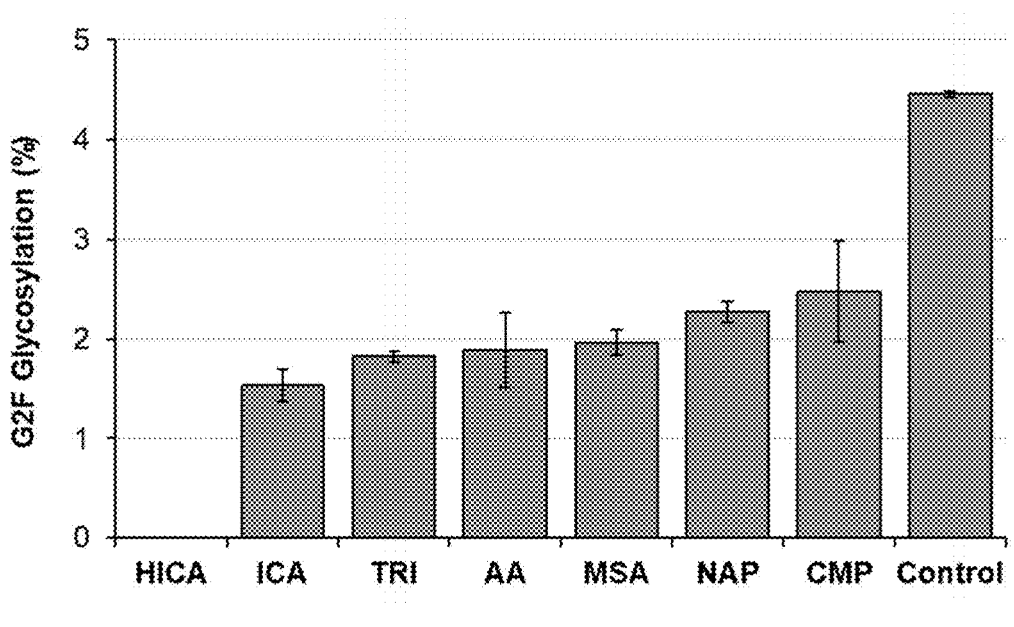
FIG. 6 shows the product quality impact on G2F, one of the glycan profile species found on IgG antibody drugs, indicating the glycosylation level. Compared to control group (column 9), AA totally inhibits the G2F formation, and all other 6 inhibitors had a significant impact on G2F formation.
Figure 7:
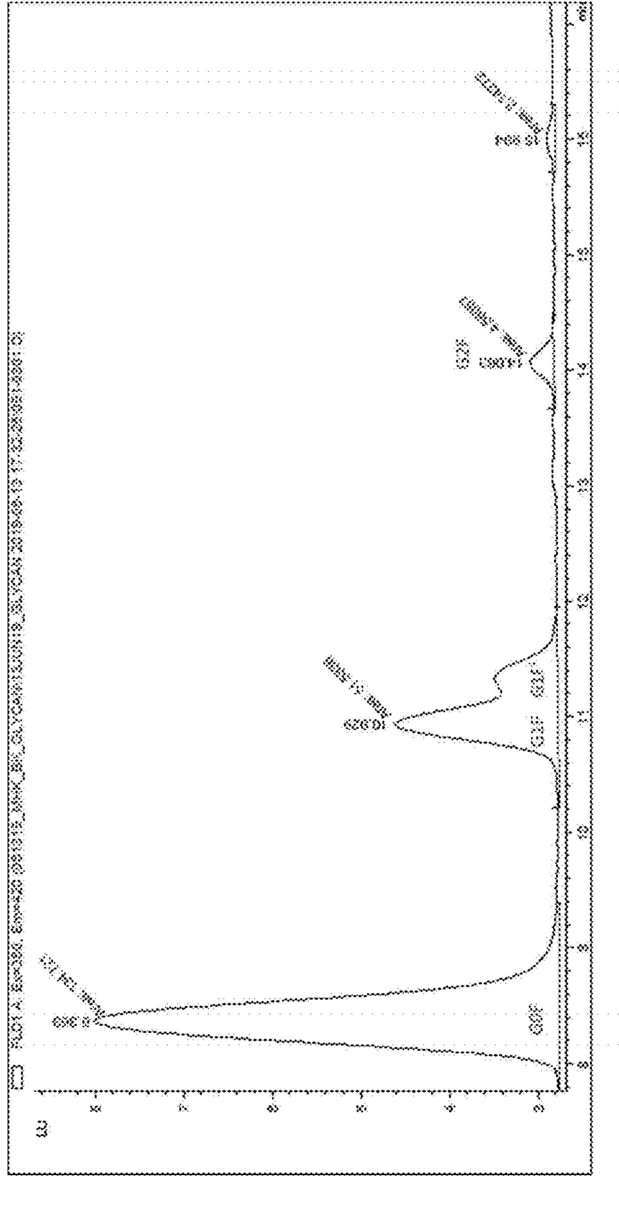
FIG. 7 shows a liquid chromatogram for control culture on Day 14. G0F, G1F, and G2F glycan profile species were observed during the bioprocess.
Figure 8:
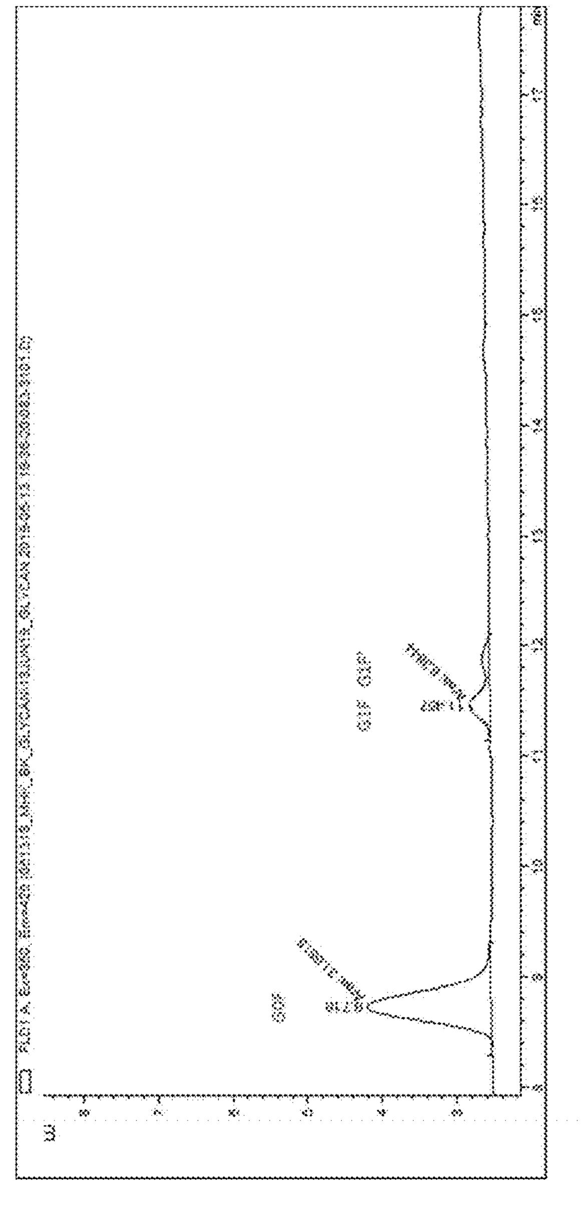
FIG. 8 shows a liquid chromatogram for an AA spiking culture on Day 14. Only G0F and G1F peaks were observed, G2F was not formed during the bioprocess.
Figure 9:
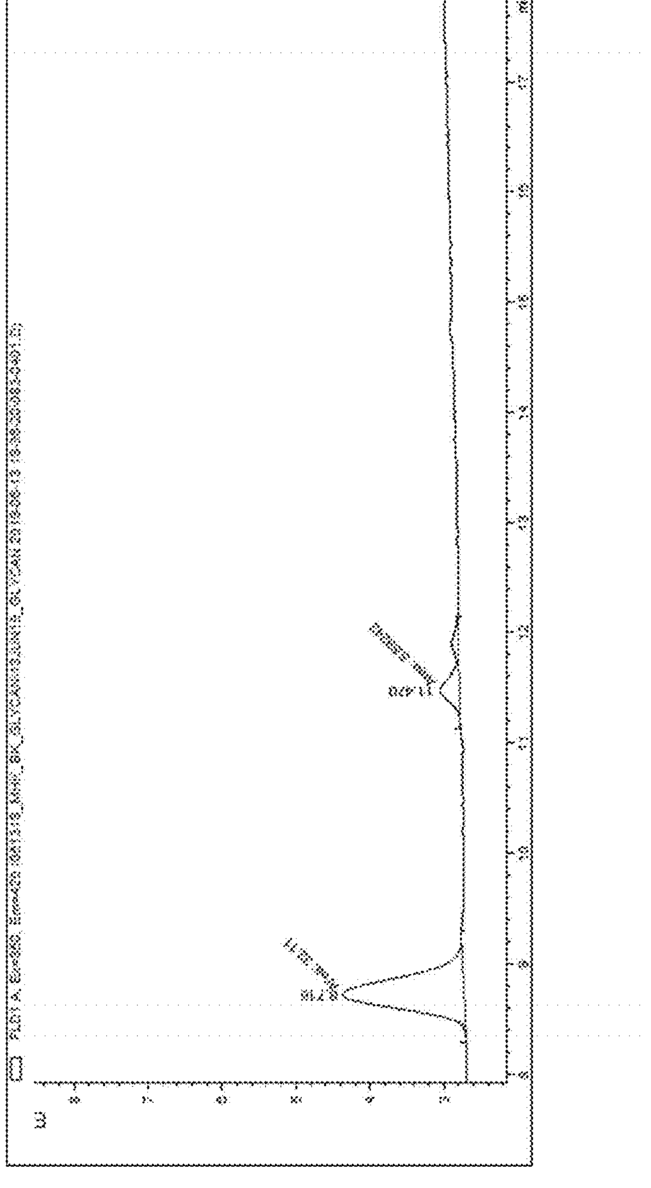
FIG. 9 shows a liquid chromatogram for an AA spiking culture on Day 14.

All 7 metabolites showed an inhibitory impact on productivity and product quality. HICA, CMP, ICA and TRI showed a strong inhibition on productivity, which is more than a 30% productivity drop compared to the control (FIG. 4). Product quality is a critical parameter for the bioprocess and drug approval, where glycan profile is one of the most important Critical Quality Attributes (CQA). AA, HICA, CMP, MSA, and ICA shown higher impact on G1F formation (FIG. 5), and AA totally inhibit the G2F formation, and all other 6 inhibitors significant impact on G2F formation (FIG. 6). Duplicated spiking experiments shown that the impact on glycan profile is consistent (FIGS. 7, 8, and 9).

Conclusions

More than 30,000 features were captured by the LC-MS metabolomics study described herein and the top 20 inhibitor candidates with high confidence in identification matching were selected by multivariate data analysis and pathway analysis. The highly ranked candidates were experimentally verified by spiking them in the batch culture, and among them 11 out of 15 showed an inhibitory impact on cell growth. Eight metabolic by-products were verified structurally and biologically. Among them, six metabolites are novel inhibitory byproducts of cell growth and/or productivity and 4 of them are first-time identified CHO metabolites (See Table 2).

TABLE 2

AA, HICA, CMP, GMP, MSA, ICA, TRI and NAP were identified as inhibitors for CHO cell process in this study. GMP and ICA were reported as a CHO cell culture inhibitor in publications/patent, and the rest of the 6 metabolites will be claimed by us. TRI, NAP, AA and MSA were first-time identified as CHO cell metabolites.

| Metabolite ID | Conc. (μM) | Pathway | Inhibitor Reported |
|---|---|---|---|
| AA | 14359 | Citric cycle | N |
| HICA | 64.09 | Leucine | N |
| CMP | 11.27 | Pyrimidine | N |
| GMP | 20 | Purine | Y |
| MSA | 13.59 | Isoleucine | N |
| ICA | 2.5 | Tryptophan | Y |

TABLE 2-continued

AA, HICA, CMP, GMP, MSA, ICA, TRI and NAP were identified as inhibitors for CHO cell process in this study. GMP and ICA were reported as a CHO cell culture inhibitor in publications/patent, and the rest of the 6 metabolites will be claimed by us. TRI, NAP, AA and MSA were first-time identified as CHO cell metabolites.

| Metabolite ID | Conc. (μM) | Pathway | Inhibitor Reported |
|---|---|---|---|
| TRI | 0.812 | NADPH | N |
| NAP | 0.196 | Arginine and proline | N |

Example 4

Accumulation of Inhibitory Metabolites in Fed Batch Culture

Fed-batch conditions were the same as CHO K-1 industrial standard fed-batch process in Example 2. Batch process conditions were the same as CHO K-1 industrial standard batch process in Example 2.

Metabolites were identified by LC-ESI-MS. Table 3 shows the identified inhibitory metabolites accumulated in the process and their accumulation after 6 days in a batch process and after 5, 8 and 14 days in a fed-batch process.

TABLE 3

Inhibitory metabolite accumulation in batch and fed batch processes

| CHO K1 | Day | AA μM | HICA μM | MSA μM | CMP μM | TRI μM | NAP μM |
|---|---|---|---|---|---|---|---|
| Batch | 6 | 1910 | 10.62 | 3.97 | 11.69 | 0.085 | 0.164 |
| Fed | 5 | 1238 | 8.53 | 1.3 | 1.14 | 0.018 | 0.096 |
| Batch | 8 | 4026 | 26.95 | 5.62 | 5.82 | 0.132 | 0.178 |
| | 14 | 14359 | 64.09 | 13.59 | 11.27 | 0.812 | 0.196 |

This example shows the inhibitor concentrations in batch culture and fed-batch culture. We conclude that the inhibitory metabolites accumulated in the major bioprocess.

Example 5

Inhibitory Metabolites Accumulation in CHO K1, CHO GS, and HEK 293 in Batch Culture Batch process conditions were the same as CHO K-1, CHO GS and HEK 293 industrial standard batch process in Example 2. Metabolites were identified by LC-ESI-MS. Table 4 shows the identified inhibitory metabolites accumulated in the process and their accumulation after 6 days in a batch process. Table 4 shows that the six inhibitory metabolites exist in different mammalian cell culture lines and accumulate in batch culture.

TABLE 4

Inhibitory metabolite accumulation in CHO K1, CHO GS, and HEK 293 in batch culture

| Conc. (μM) | AA | HICA | MSA | CMP | TRI | NAP |
|---|---|---|---|---|---|---|
| CHO K1 | 1910.00 | 10.62 | 3.97 | 11.69 | 0.09 | 0.16 |
| CHO GS | 717.42 | 31.63 | 2.59 | 78.51 | 0.81 | 0.20 |
| HEK 293 | 984.53 | 53.80 | 1.55 | 2.43 | 0.02 | 0.17 |

From the accumulation at the end of batch culture we conclude that the inhibitory metabolites widely exist in the mammalian cell lines.

Example 6

Process Development to Mitigate the Inhibitory Metabolites Accumulation

The transfection of regulatory genes for the production of inhibitory metabolites into CHO K1 cell line in the batch culture mitigates the growth of inhibitory metabolites.

The purpose of transfection is to overexpress regulatory genes/enzymes for the inhibitory metabolites. The downstream enzyme-coded genes were knocked into a CHO cell line through the constructed plasmids with Got1, Hoga1, Cat, Slc35a1 on pcDNA 3.1 (+) vector (V79020, ThermoFisher Scientific). The plasmids were amplified using 5-alpha competent *E. coli* (C2987I, New England BioLabs). Polyethylenimine (408727, Millipore Sigma) was used to transfect the plasmids into the mammalian cell lines to mitigate the concentration of the inhibitory metabolites by overexpressing the regulatory genes for the inhibitory metabolites. The transfection was done the same as CHO K1 industrial standard batch process, except that the initial inoculation cell density is 1 million cells/mL.

Figure 11:
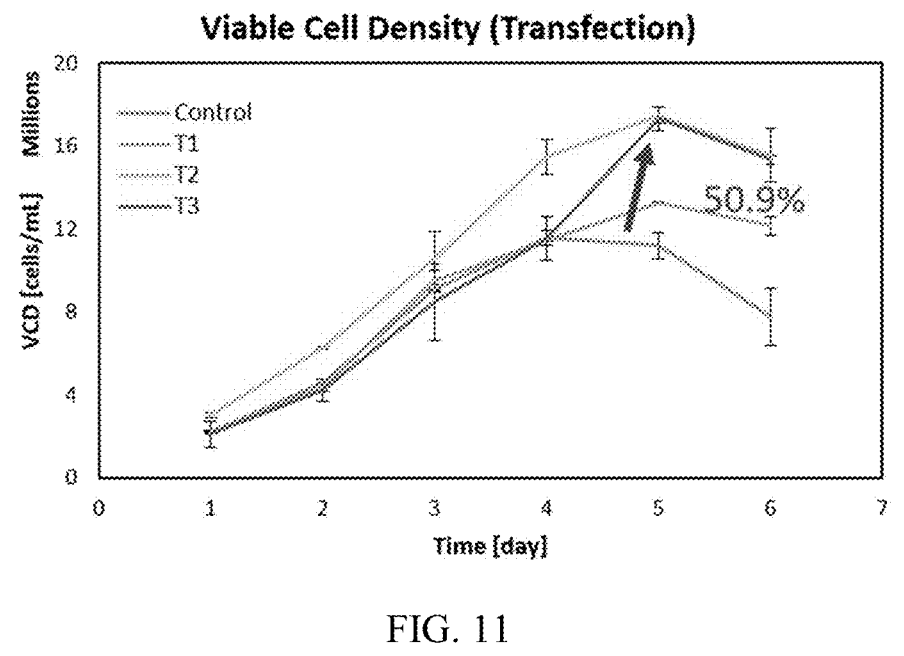

In Table 5 and FIG. 11, Control indicates a CHO K1 batch cell culture control condition without transfecting any gene; T1 indicates the cell growth profile with Got1 transfected into CHO K1 cell line; T2 indicates Got1 and Hoga1 transfection; and T3 indicates Got1, Hoga1, Cat, and Slc35a1 transfection. As shown in Table 5 and FIG. 11 comparing to the control cell culture, the concentration of all the inhibitory metabolites decreased with overexpressing Inhibitory metabolites regulation genes into CHO K1 cell line, and the growth profile is improved.

TABLE 5

Transfection of Inhibitory metabolites regulation genes into CHO K1 cell line in the batch culture.

| Clones | Culture days | AA μM | HICA μM | MSA μM | CMP μM | TRI μM | NAP μM |
|---|---|---|---|---|---|---|---|
| Control | 1 | 0.000 | 0.000 | 0.007 | 0.000 | 0.006 | 0.044 |
| T3 | 1 | 0.000 | 0.000 | 0.010 | 0.000 | 0.004 | 0.000 |
| Control | 3 | 1026.918 | 10.696 | 0.865 | 1.720 | 0.021 | 0.158 |
| T2 | 3 | 984.457 | 3.826 | 0.619 | 1.692 | 0.019 | 0.178 |
| T3 | 3 | 874.268 | 2.786 | 0.405 | 0.978 | 0.001 | 0.072 |

TABLE 5-continued

Transfection of Inhibitory metabolites regulation genes into CHO K1 cell line in the batch culture.

| Clones | Culture days | AA µM | HICA µM | MSA µM | CMP µM | TRI µM | NAP µM |
|---|---|---|---|---|---|---|---|
| Control | 5 | 1910.126 | 10.686 | 3.966 | 11.687 | 0.044 | 0.165 |
| T2 | 5 | 1868.026 | 9.951 | 2.868 | 9.433 | 0.042 | 0.129 |
| T3 | 5 | 1277.005 | 9.173 | 2.296 | 5.005 | 0.030 | 0.113 |

From this data we conclude that the inhibitor concentration decreased after the transfection of inhibitory metabolites regulation genes into CHO cell line.

Example 7

Method Development Through Pathway Analysis Coupled with Genome Scale Modeling Screening of target genes was carried out through batch mode cultivation of CHO cells under standard settings and operating conditions (no perturbation). The concentration of key nutrients including essential amino acids and glucose accumulated/depleted in the extracellular environment throughout the culture duration was continuously measured via LC-MS, through which respective metabolic uptake fluxes were calculated for constraint inputs in GEM of CHO-K1 cells line. Flux balance analysis was then performed with the objective function to maximize biomass to establish a baseline assessment on growth and biomass productivity. Subsequently, each gene encoded in the gene library included in the model was upregulated which allowed re-assessment of the objective function at the end of each successful iteration. The outcome of the study observed a number of genes that showed improvement in productivity towards biomass, which suggested internal fluxes have been efficiently re-allocated towards energy production for growth while decreasing the generation of wastes and metabolic by-products. Ultimately, by coupling computer-aid simulation work with the identification result obtained in reported publication where by-products metabolites were biologically confirmed to suppress growth in CHO culture, genes that were characterized to both contributing to the bioprocess by promoting growth in terms of biomass when compared to the established baseline, and also involving in biochemical processes that consumes the identified metabolites—were considered further for genetic engineering verification study.

Materials and Methods

Plasmid construction for inhibitory impact control verification. Biological verification on the control strategy towards accumulation of metabolites was done via transient transfection. An overall detailed strategy for subclone development and gene functionality analysis was shown in. Forward and reverse cloning primers were designed for each corresponding GOI. To ensure the expression of the enzymes, pCMV promoter is engineered into the plasmid to promote transcription. Additionally, Kozak sequence was added to promote translation activity. All plasmids with restriction enzymes and primers incorporated in this study are shown in

TABLE 6

Detailed Workflow for Subclone Development and Gene Functionality Analysis. The gene of interest (GOI) was initially cloned from CHO DNA genome, after which each GOI was subjected to the following steps of genetic engineering work for gene functionality analysis in CHO cells.

| | Steps | Objective |
|---|---|---|
| Construction of GOI | 1. PCR | Amplification of GOI |
| | 2. Gel electrophoresis | Purification of GOI |
| | 3. RE cutting | Construction of GOI into plasmids |
| | 4. RE ligation | Construction of GOI into plasmids |
| Transfection of GOI | 5. Transformation with *E. coli* | Amplification of constructed plasmids |
| | 6. Extraction | Plasmid purification and extraction |
| | 7. Transient transfection | Expression of GOI in mammalian cells |

Construction of plasmid vector. CHO-K1 cells were extracted from Day 4 to Day 6 of fed-batch culture. Isolation and purification of CHO-K1 RNA was conducted with using RNeasy Mini Kit from Qiagen USA (Germantown, MD). Quantification of RNA concentration was performed on NanoDrop OneC from Thermo Fischer Scientific (Waltham, MA). Construction of CHO-K1 cDNA library obtained was performed utilizing SS3 superscript kit from Invitrogen (Carlsbad, CA). PCR amplification was conducted on cDNA previously extracted. The GOI include Adh5, BCat1, Cat, Got1, Hadhb, Hoga1, Slc35a1. Primers were designed based on the gene sequences obtained from NCBI database (Appendix A) and the plasmid restriction enzymatic sites. Detail information regarding primer sequences is shown in Table 7. PCR was conducted to amplify GOI using Q5® High-Fidelity DNA Polymerases from New England Biolabs (Ipswich, MA). PCR products were purified with DNA gel electrophoresis at 100 V for eighty minutes and QIAquick Gel Extraction Kit from Qiagen USA (Germantown, MD). Complex GOI/plasmid was constructed using GOI and pcDNA3.1/Zeo(+) plasmid from Invitrogen (Carlsbad, CA). Complex GOI/plasmid was further digested with restriction enzymes from New England Biolabs (Ipswich, MA). After dephosphorylation of 5' end of plasmid using Quick CIP from New England Biolabs (Ipswich, MA), complex GOI/ plasmid was ligated with using T4 DNA Ligase from New England Biolabs (Ipswich, MA).

TABLE 7

Primer Sequences Designed for PCR Amplification. In this study, seven genes were studied for enzymatic activities upon up-regulation due to transient transfection, of which the specific primer sequences for each forward and reverse primer are noted.

| Gene Name | Primers | Res. Enzvme | Primer Sequence 5'-3' | SEQ ID NO |
|---|---|---|---|---|
| Adh5 | Forward | AflII | taatatatac ttaaggccac catggcgaac caggtgat | 1 |
| | Reverse | EcoRI | cggccggaat tcttacagct ttagaacagt | 2 |
| Bcat1 | Forward | AflII | taatacttaa ggccaccatg gaclgcagta at | 3 |
| | Reverse | EcoRI | gcccgaattc tcacgataac aagattg | 4 |
| Cat | Forward | AflII | atatcttaag gccaccatga tgcgatttct tac | 5 |
| | Reverse | EcoRI | gcgccglcta gattatcaca ggtlagcttt tt | 6 |
| Got1 | Forward | AflII | atacttaagg ccaccatgtc gcctccgtca gtc | 7 |
| | Reverse | XbaI | ggcgctctag attatcactg gattttggtg acagc | 8 |
| Hadhb | Forward | AflII | tatacttaag gccaccatgt ctaccatctt gactt | 9 |
| | Reverse | EcoRI | ccggaattct cattttggat aagcttcc | 10 |
| Hoga1 | Forward | AflII | atatcttaag gccaccatgc taggccccca gatgt | 11 |
| | Reverse | XbaI | gcgctctaga ttatcagagc cagccattgt tgctg | 12 |
| Slc35a1 | Forward | HindIII | tatataccca agcttgccac catggctcag gcgagagaaa at | 13 |
| | Reverse | XbaI | gcgcgcgctc tagattatca cacaccaatg actc | 14 |

Plasmid transformation. Bacteria transformation was conducted using 50 µl of NEB® 5-alpha competent *E. coli* cells from New England Biolabs (Ipswich, MA) with 5 µL of previously ligated plasmids. Cells were mixed carefully by gently tapping on mixing tube five times and was incubated on ice for 30 minutes. Cells were heat shocked using dry bath from Fisher Scientific (Waltham, MA) to heat shock the cells at 42° C. for thirty seconds and cells were incubated back on ice for five minutes. A total volume of 950 µL of SOC Outgrowth Medium from New England Biolabs (Ipswich, MA) was added to the cells and the total mixture were transferred to 50 mL centrifuge tubes from VWR (Radnor, PA). Tubes were slightly capped in order to allow cell respiration and incubated for ninety minutes in a humidified, shaking incubator from Queue Systems Inc (Columbia, SC) operated at 250 RPM and 37° C. A total volume of 100 µL cells were uniformly and gently spread using a disposable inoculating loop from VWR (Radnor, PA) onto a LB agar ampicillin plate from Sigma Aldrich (St. Louis, MO) previously warmed to 37° C. Cells were incubated overnight at 37° C.

Colonies (approximately three to four) were selected after the incubation period and were mixed with 5 mL of LB broth medium from Sigma Aldrich (St. Louis, MO) and 5 µL of ampicillin in 50 mL centrifuge tubes from VWR (Radnor, PA). Tubes were slightly capped to allow cell respiration and incubated for 12 hours in a humidified, shaking incubator from Queue Systems Inc (Columbia, SC) operated at 250 RPM, 32° C. Plasmid extraction was performed using ZymoPURE II Plasmid Midiprep Kit from Zymo Research (Irvine, CA) after twelve hours of incubation. Cell pellets were isolated by centrifuge from Eppendorf (Hamburg, Germany). Plasmid concentration (in the range of $ng \cdot \mu L^{-1}$) was measured using NanoDrop from Thermo Fischer Scientific (Waltham, MA). For validation process, restriction enzymes were used to cut and validate the GOI followed by gel electrophoresis.

LC-MS/MS method for metabolites profiling: Standards of metabolites were purchased from Sigma Aldrich (St. Louis, MO) and used for identification of wasted inhibitor metabolites. Operating parameters and samples preparation protocol were followed to a previously published protocol.

Cells, Media and Supplements: A CHO-K1 cell line expressing IgG (VRC01) antibody obtained from NIH (National Institute of Health) was used for this study with two proprietary media. The conditions for inoculation and cultivation of cells were followed to a previously published protocol.

Results and Discussion

Pathway analysis of CHO metabolism. Global metabolomic analysis on different modes of CHO bioprocess identified eight different growth by-products which accumulated throughout the entire culture duration of cells. However, although the growth inhibitory effects due to presence of these metabolites in the CHO extracellular environment has been verified, the corresponding pathway and the extent through which their nutrient precursors are metabolized currently is unknown. A strategic methodology was thus developed via pathway analysis coupled with GEM to control the extent through which the growth inhibitory metabolites are accumulated in CHO bioprocess. Metabolic pathway analysis was conducted on each metabolite via GEM, after which metabolites were mapped to a holistic regulatory metabolic network. First, all metabolic enzymes capable of either direct/indirect catabolizing of toxic metabolites or re-allocating metabolic fluxes into alternative metabolic branches not generating by-products inhibitors were considered. The control of the accumulation of inhibitors by upregulating the expression of identified candidate genes responsible for modulation of such enzymes was evaluated. The list of candidate genes was further biologically verified through genetic engineering work for assessment of the outcome impact on growth. The final list of genes through which upregulation of enzymatic activities can promote production towards growth, the related metabolic pathways, and the corresponding input metabolites are shown in Table 8.

TABLE 8

Genes, Corresponding Metabolic Pathways and Regulated Downstream Metabolites. Genes and pathways functionalities were reported from previous work studied on different mammalian cell lines. In this study, genes were inserted into plasmids and transiently transfected into cells when cells reached viable cell density of $1 \times 10^6$ cells · $mL^{-1}$.

| Genes | Related Metabolic Pathways | Regulated Metabolites |
|---|---|---|
| Adh5 | Leucine metabolism[1] | HICA, MSA |
| Bcat1 | Leucine, isoleucine metabolism[2] | HICA, MSA |
| Cat | Tryptophan metabolism[1] | TRI |
| Got1 | Glutamate/glutamine metabolism[3], arginine/proline metabolism[3], aspartate metabolism[3] | TAA, CMP, NAP, TRI |
| Hadhb | Isoleucine metabolism[1] | HICA, MSA |
| Hoga1 | Arginine/proline metabolism (UK) | CMP, TAA, NAP |
| Slc35a1 | Pyrimidine metabolism[2] | CMP |

[1]enzyme controls other metabolic fluxes that consumes the metabolites.
[2]downstream enzyme involves in biochemical process that utilizes metabolites as input reactants.
[3]reported to be involved in the metabolic pathways, but the exact relationship is understudied.

Engineering strategy targeting the accumulation of metabolites. Pathway analysis conducted on HICA and MSA revealed their pathway of origin stemming from the catabolism of BCAA. In the first step of the catabolism, transfer of an α-amino group from each of the precursor amino acid (leucine, isoleucine, and valine) yields three different respective branched-chain α-ketoacids. Deamination of leucine is catalyzed by amino acid transferase to transfer the amino group in leucine to α-keto acid acceptor in α-ketoglutarate. Other BCAA (e.g., valine and isoleucine) also share the same property of being α-keto acid acceptor as leucine. Further analysis revealed HICA to be the end-product of the leucine metabolism, specifically through the direct conversion of keto acid into hydroxyl acid. Therefore, regulation over the accumulation of α-ketoisocaproic acid (MC) serves as the main strategy in modulating metabolic fluxes into formation of HICA, as illustrated in FIG. 12. Specifically, by re-distributing the fluxes converting α-ketoglutarate to glutamate to other BCAA would effectively decrease the presence of α-ketoglutarate at a given time that can participate in the conversion of leucine to KIC. Therefore, up-regulation of cytosolic BCAA transaminase (BCAT1) is one effective approach to control HICA generation. An argument could be made where reducing KIC could compensate the fluxes available going into the generation of acetyl-CoA, which is a crucial substrate for energy generation throughout the Krebs cycle. While that remains true regarding the amount of acetyl-CoA generated by catabolism of leucine, it is important to note that acetyl-CoA can also be generated from the catabolism of isoleucine, or from the conversion of succinyl-CoA, and thus down-regulating the degradation pathway of leucine would generate less amount of HICA metabolites as by-products.

Additional pathways were also studied via GEM. In CHO cells, alcohol dehydrogenase (ADH5) catalyzes the extracellular transport reaction involving formaldehyde and glutathionate. Investigation into glutathionate through GEM reveals key reactions mapping glutathionate to MC via the leucine metabolism pathway involved in pathway 1 and pathway 2, as illustrated in FIG. 12. For pathway 1, glutathionate participates in the reaction generating cysteine from cystine which is a by-product from the transporting reaction of allocating cytoplasm leucine to extracellular leucine. For pathway 2, through the glutathionate metabolism, glutamate is generated which serves as a participating metabolite in the generating reaction of MC. Up-regulation the activity of ADH5 further metabolizing glutathionate into formaglutathionate, reducing the amount of glutathionate available for participation in other reactions generating complimentary substrates (decreasing the amount of leucine generated which can metabolized into MC for pathway 1, or decreasing the amount of glutamate which can catalyze the reaction generating MC for pathway 2).

As previously noted, tryptophan serves as the main substrate for nicotinamide metabolism, which generates metabolite TRI as a by-product (FIG. 13A). Proline, while mainly metabolizing into pyruvate as the main substrate for the TCA cycle, also generates NAP as a by-product (FIG. 13B). Metabolite TAA, on the other hand, is a direct waste product result from the TCA cycle (FIG. 13C). CMP is the main metabolite participating in pyrimidine metabolism (FIG. 13D). Up-regulation of CAT through the metabolism of tryptophan and nicotinate/nicotinamide (targeting metabolite TRI), GOT1 and HOGA through the metabolism of proline (targeting metabolite NAP), GOT1 through the metabolism of glutamate and TCA cycle (targeting metabolite TAA), and SLC35A1 through the biosynthesis of N-glycans allows control strategy over the accumulation of identified metabolites.

Figure 14A:
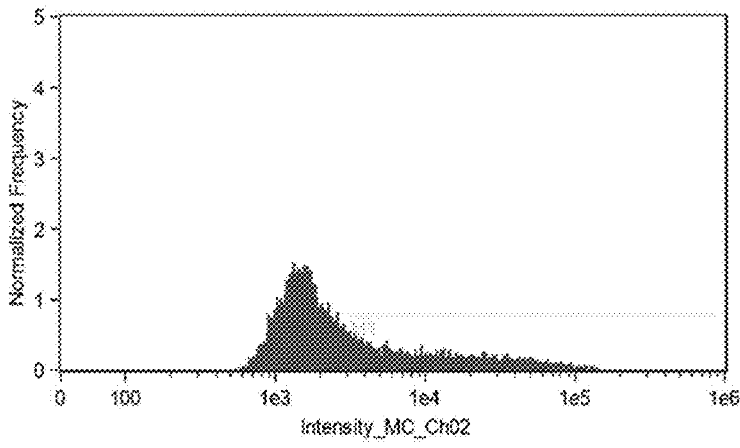
FIG. 14A-B show transfection efficiency indicated through GFP plasmid transfection. Here, cellular physiology of CHO-S cells at Day 2 (FIG. 14A) and Day 3 (FIG. 14B) post transfection was assessed by flow-cytometric assay. Results indicated increase in gene expression during peak production period in CHO-S cell lines.
Figure 14B:
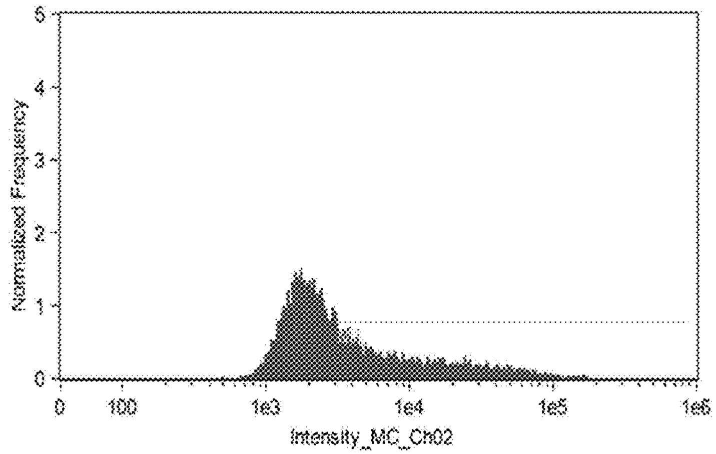
Figure 15:
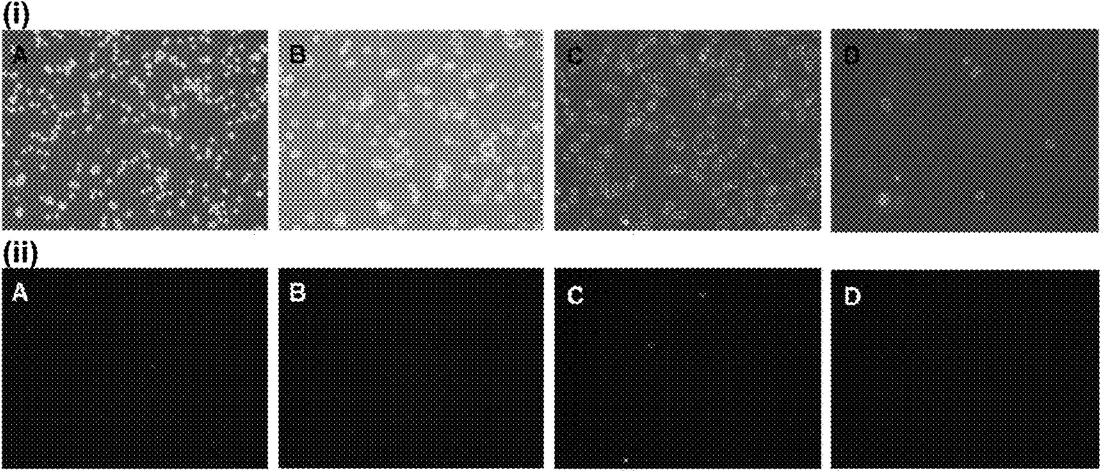
FIG. 15 shows CHO-S cells visualized under fluorescence microscope. (i) Imaging of cells at regular lighting condition. (ii) Imaging of cells visualized under fluorescence light. Shown in (i) and (ii): (A) Day 2, transfected cells with GFP engineered plasmids, (B) Day 2, control cells without plasmid insertion, (C) Day 3, transfected cells with GFP engineered plasmids, (D) Day 3, control cells without plasmid insertion.

Plasmid transfection efficiency assessment. The GFP gene was utilized as reporter of expression during translation to assess the transfection efficiency. Plasmid engineered with GFP gene was inserted into CHO-S cell line and the fluorescence intensity was assessed through fluorescence microscopy and flow cytometry. A wild-type condition was used as the control for the transfection conditions. Cells for both the control and transfection were derived from the same culture to eliminate variation in growth cycle and other culture conditions. Comparison of fluorescent intensity measurement post-transfection on Day 2 and Day 3 for each of the transfected and control conditions is shown in FIG. 14. CHO-S cell lines showed 35.2% transfection efficiency on Day 2 with the supplied media and specific culture conditions (see Materials and Methods above). On Day 3, the measured efficiency increased to 43.1%, which demonstrated that cells have successfully expressed GFP during CHO-S production period. The results were also confirmed through fluorescence microscopic imaging, as cells also exhibited high degree of fluorescence markers when visualized under fluorescence light, as shown in FIG. 15.

Quantification of expression level of transfected gene of interest through qPCR. The expression level of seven different genes transfected into CHO-S cells were evaluated using relative quantification (RQ) compared to the calibrator. The study was divided into eight unique subclone groups. Each subclone was overexpressed with an individual GOI via transient transfection at plasmid concentration of 50 $\mu g \cdot \mu L^{-1}$ to cells, with an additional gene mix subclone group where all seven genes were transfected to cells at once, but at lower individual plasmid concentration found in the individual case (6.25 $\mu g \cdot \mu L^{-1}$ per gene, total of plasmid concentration of 43.75 $\mu g \cdot \mu L^{-1}$ for seven genes). A negative control was included in the study where no genetic engineering work involving plasmid transfection occurred. Each subclone was cultured for 6 days. Cells for both the control and transfection subclones were derived from the same culture to eliminate variation in growth cycle and other culture conditions. Plot graphs of RT-qPCR result are shown in FIG. 16A-G. It was clear that the level of gene expression from the control was the lowest in all cases, followed by the gene mixture condition where each gene was transfected at 6.25 $\mu g \cdot \mu L^{-1}$ per gene with total of plasmid concentration of 43.75 $\mu g \cdot \mu L^{-1}$ for seven genes, as compared to 50 $\mu g \cdot \mu L^{-1}$ of plasmid concentration found in the individual case. The range of the obtained RQ values showed considerable variability among each different transfected condition when compared against the gene mixture condition, and vice-versa for the control. Thus, the study suggests that all engineered plasmids, although individually exhibited a different level of gene expression when inserted into cells depending on the GOI, all show higher level of gene expression versus the negative control from samples obtained at Day 3 where most of the gene expression in batch culture of CHO cells occur, which serves as clear indication that plasmids were successfully transfected into cells and all GOI were expressed during the CHO translation process.

Gene functionality study through metabolic pathway analysis. As mentioned previously, HICA is generated as the downstream metabolite from the metabolism of leucine in mammalian cells, of which cellular biochemical activities are regulated by ADH5 and BCAT1 enzymes. A total of seven genes, all of which were transfected individually into cells at plasmid concentration of 50 $\mu g \cdot \mu L^{-1}$ were compared with a gene mix subclone group where all seven genes were transfected into the cells at once, but at lower individual plasmid concentrations (6.25 $\mu g \cdot \mu L^{-1}$ per gene, total of plasmid concentration of 43.75 μg·μL−1 for seven genes) than were used when each gene was transfected individually. A negative control was included in the study where no genetic engineering work involving plasmid transfection occurred. The results are shown in FIG. 17A-G.

Figure 17A:
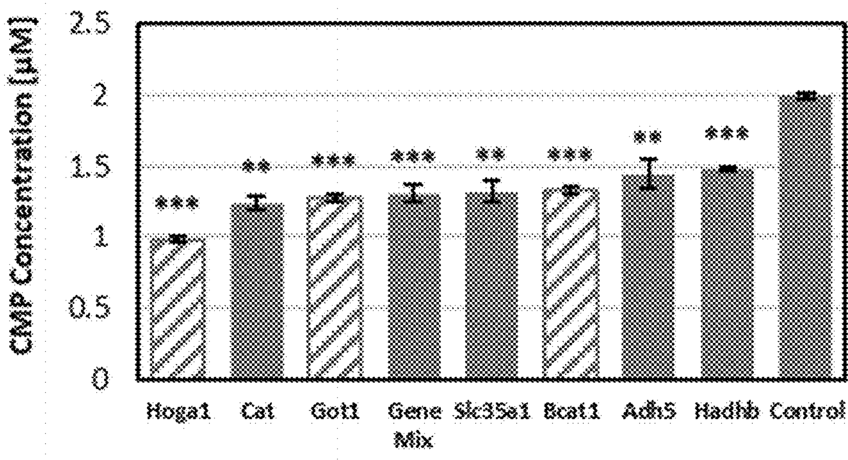
Figure 17B:
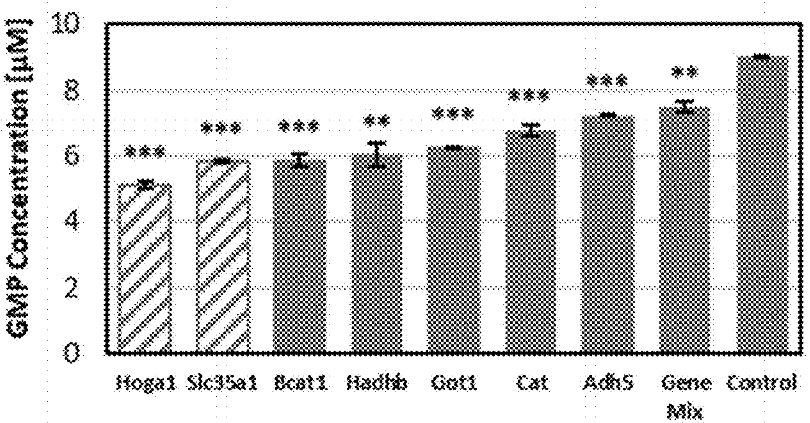
Figure 17C:
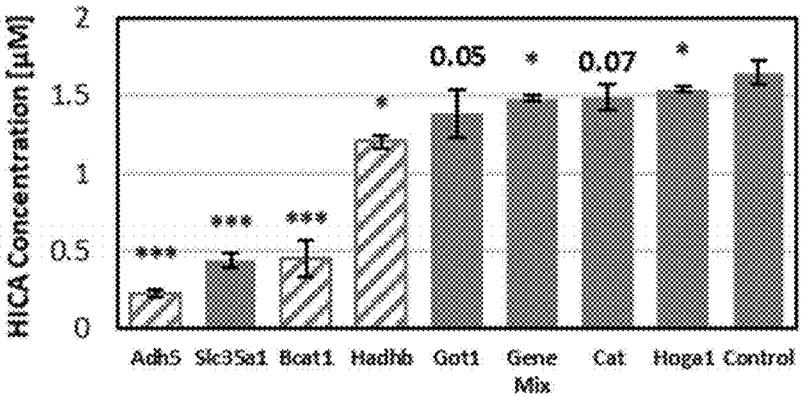

Clones that were transfected with Adh5 and Bcat1 showed decrease in HICA accumulation by 86.13% and 72.31%, respectively (see FIG. 17A). With regards to the metabolism of branched amino acids (BCAA), isoleucine metabolism pathway actively interacts with leucine metabolism pathway (see FIG. 12). Through the overexpression of Hadhb gene in CHO cells, the study showed that HICA accumulation in CHO was decreased by 27.05% (FIG. 17C) when compared against the control, suggesting that cellular metabolic fluxes have been re-allocated internally more towards the metabolism of isoleucine and subsequently, less towards the generation of growth inhibitory by-products (in this case, HICA).

With regards to TRI, the metabolite is part of the metabolism of nicotinamide and was generated as the downstream product from the metabolism of NAD and NADH, of which nicotinamide is the upstream precursor. In this study, clones that were overexpressed with Cat and Got1 genes showed decrease in the accumulation of TRI by 27.8% and 40.43%, respectively (see FIG. 17B). Further, clones overexpressing Got1, Hoga1 and Slc35a1 genes showed decrease in the accumulation of CMP by 35.68%, 33.59% and 50.63%, respectively (see FIG. 17C). Thus, the data suggest that cells have re-distributed internal metabolic fluxes into the metabolism of glutamine, pyrimidine, arginine, and proline and less towards the generation of growth inhibitory by-products (in this case, CMP).

Overall, the results indicate that HICA, TRI, and CMP are metabolic by-products generated through the metabolism of BCAA, tryptophan, glutamine, and pyrimidine in CHO system as similar to other mammalian host cells. Additionally, through genetic engineering work by overexpressing of upstream genes that involved in different metabolic pathways, the study also showed that up-regulation of the translation activity of metabolic enzymes, including ADH5, BCAT1, CAT, GOT1, HOGA1 and SLC35A1, can control the generation of growth inhibitory metabolites, either by increasing the fluxes of biochemical reactions that metabolize waste by-products (downstream enzyme to the generation of waste), or re-allocating the available metabolic fluxes into other alternative metabolic pathways.

Interestingly, the accumulation of HICA in CHO culture showed a significant decrease when the pyrimidine transporter gene Slc35a1 was overexpressed (73.51% less accumulation compared against the control, see FIG. 17A). Additionally, up-regulating Bcat1 and Hadhb 1 also decreased the accumulation of TRI by 42.96% and 35.38%, respectively. The data thus suggests that SLC35A1, BCAT1, and HADHB1 enzymes potentially interact with the generation of HICA and TRI via understudied metabolic pathways. The results also show that in most cases, overexpressing metabolic genes decreases the accumulation of CMP when compared against the control, which suggests that pyrimidines interact with many different metabolic pathways of amino acids.

Figure 17D:
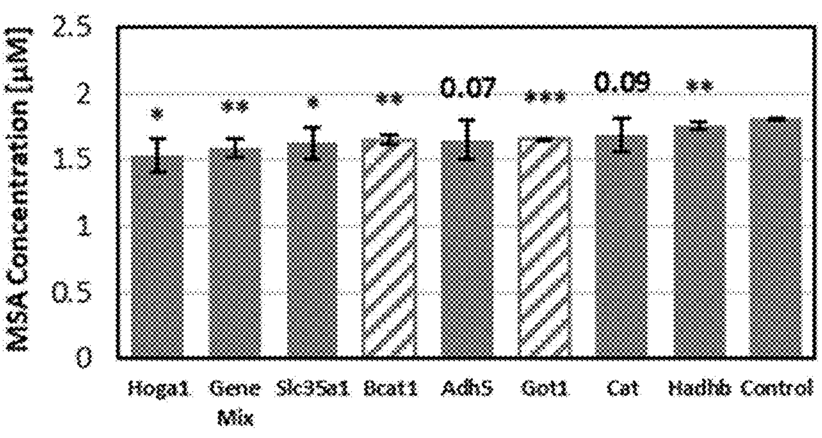
Figure 17E:
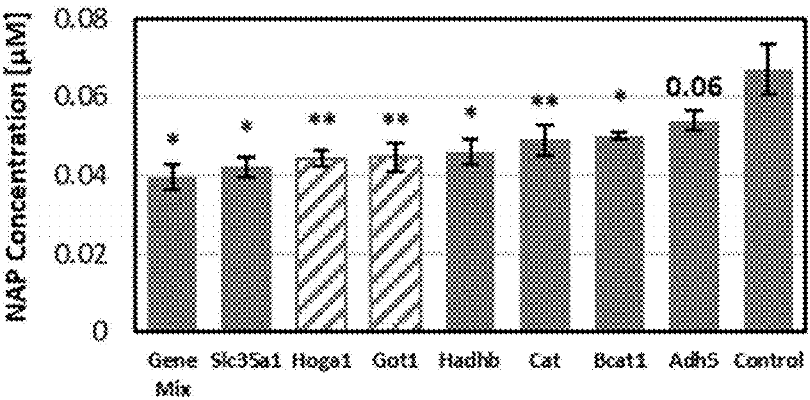
Figure 17F:
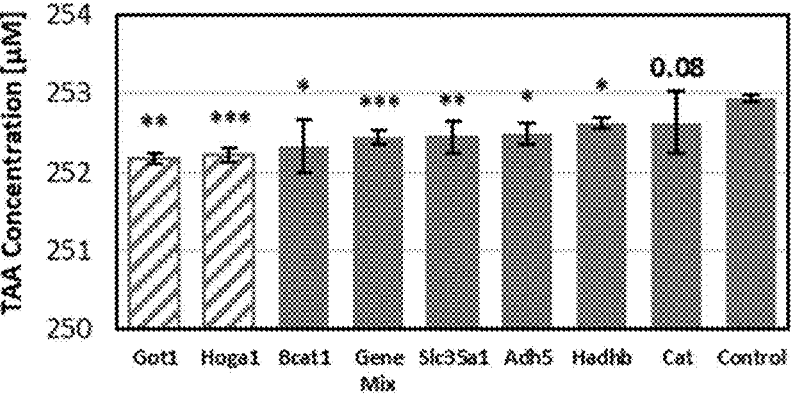

The results also revealed that accumulation in the concentrations of TAA, MSA, and NAP at harvest in all subclones did not show a significant difference when compared against the control (see FIGS. 17D, E, and F). Without being limited by theory, it is hypothesized that these metabolites do not derive from the reported metabolism pathways as in other mammalian cell lines (see Table 7). Thus, genetic intervention of the corresponding genes responsible for glycolysis and/or proline and isoleucine metabolism pathways could perhaps offer a more robust set of tools to develop the proper control strategy and manipulate the generation of these growth inhibitory metabolites.

Assessment of culture performance. The growth profile of all individual subclone is shown in FIG. 18A-B. Additionally, the effect of up-regulation of all engineered vectors (seven genes) transfected into CHO-S cells line at a concentration of 6.25 $\mu g \cdot \mu L^{-1}$ per gene was also studied (see FIG. 19). In both cases, cells were cultivated in batch mode until the viability of cells dropped below 80%. Overall, all subclones (individual gene as well as genes mix) with overexpression of metabolic genes showed promotion in growth when compared against the control. The results altogether suggest that CHO cellular growth in bioprocesses can be improved, either by increasing the generation of cellular energy utilized towards growth by metabolizing growth inhibitory metabolites as reactants in some understudied biochemical pathways (and therefore reducing their accumulating concentration) or re-distributing metabolic fluxes into alternative metabolism pathways that do not generate metabolic by-products that can suppress cellular proliferation.

Nutrient consumption profile. The nutrient consumption profile of all transfected subclones is shown in FIG. 20A-G. Overall, cells across all conditions consumed highest amount of nutrients during Day 4 of batch culture. Overall, the consumption profile of key exchange ions including sodium and potassium from the transfected subclone is generally higher when compared against the control. Traditionally, cells utilize the $Na^{+}/K^{+}$ pump transport mechanism to regulate water balance and other cellular physiological state. It is speculated that the higher uptake rate of ions promotes the activity of key nutrient exchange gradient, which suggests that cells exhibit a more rapid substrate utilization and metabolic activity rate when key target biochemical pathways capable of direct/indirect catabolizing identified metabolites are up-regulated. This further translates to a higher accumulation profile of ammonia and lactate, as measured on Day 4 and Day 6 of the batch process (see FIGS. 20C and 20D). However, peak viable cell density (VCD) and cumulative integral viable cell density (IVCD) across all conditions was not observed to be lower, as illustrated in FIG. 18A-B where all engineered subclones show better culture performance compared to the control. Interestingly, all transfected subclones showed a higher glucose consumption profile across the entire culture duration (less glucose accumulated, see FIG. 20D), with an even more aggressive consumption profile starting from Day 4 to Day 6. When comparing the nutrients consumption profile (see FIG. 20A-G), this culture period aligns with the production phase of cells, and thus the improved performance in cellular growth (higher cell density) allows cells to utilize more glucose towards proteins production. The results obtained from different cellular activity profiles suggest that the productivity of cells was also up-regulated due to the higher glucose consumption profile during production phase as cells utilize glucose predominantly to produce glycans. Future studies addressing the titer profile of cells post transfection can be conducted to analyze the productivity of CHO subclones with promoted growth while producing less toxic growth inhibitors. Interestingly, the measured concentration of glutamine at Day 4 from the Got1 subclone is significantly higher when compared against the control. Traditionally, GOT1 enzyme catalyzes the biosynthesis of glutamate from aspartate and cysteine. It could be speculated that up-regulation of Got1 induces more glutamate being generated, which could be converted to glutamine through the glutamine synthesis pathway regulated by glutamine synthetase. Nevertheless, future studies regarding genetic intervention of the studied genes responsible for these metabolic pathways is needed to better explain the observed trend in nutrient exchange profile.

Figure 19A:
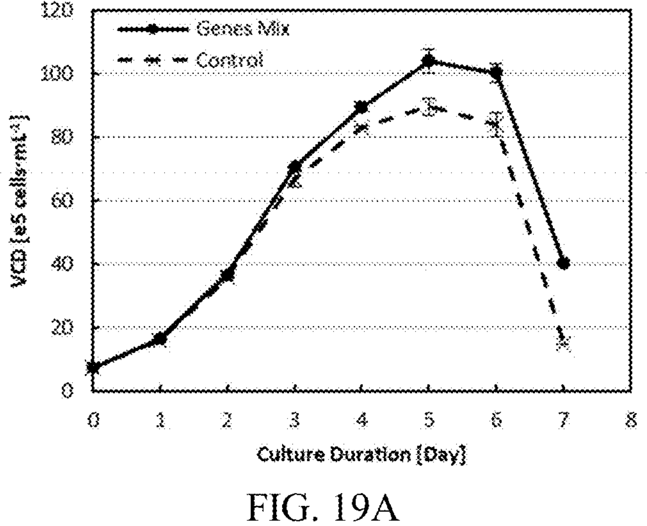
FIG. 19A-B are graphs showing the growth profile of multi-gene transfected subclones.
Figure 19B:
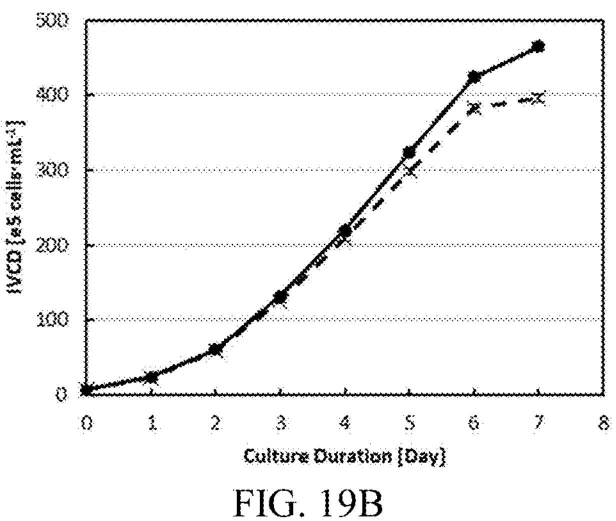
Figure 20A:
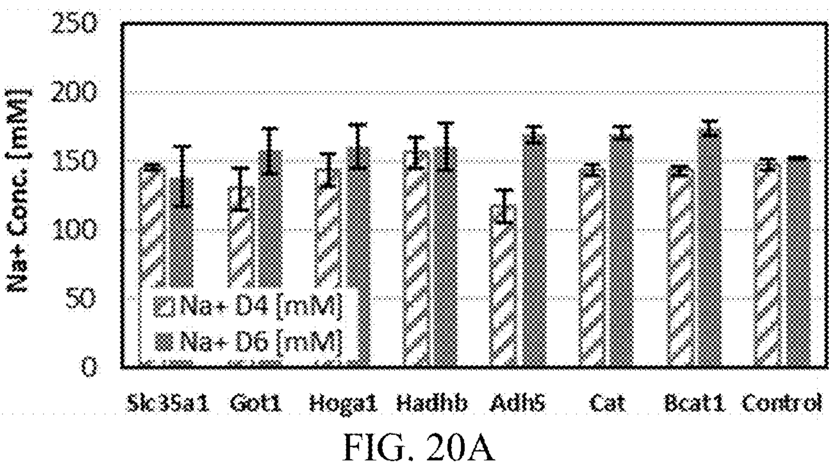
FIG. 20A-G are graphs showing the nutrient uptake profile of individual transfected subclones.
Figure 20B:
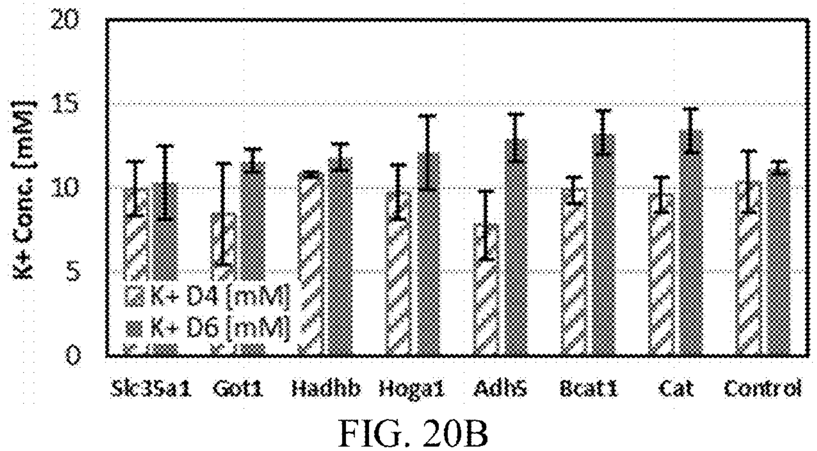
Figure 20C:
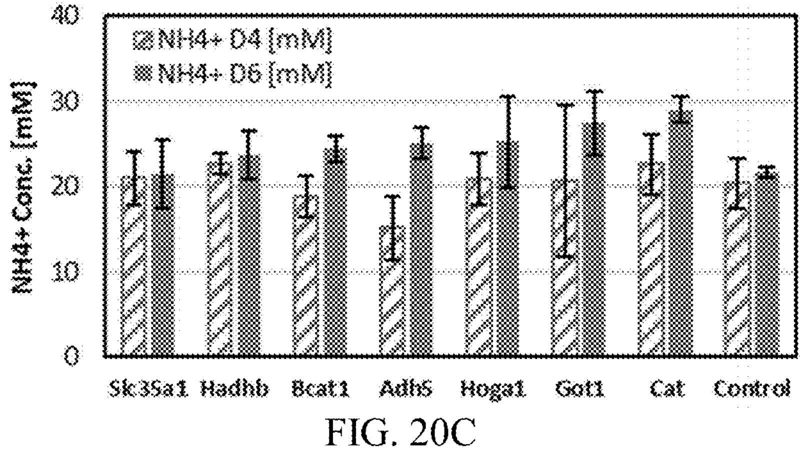
Figure 20D:
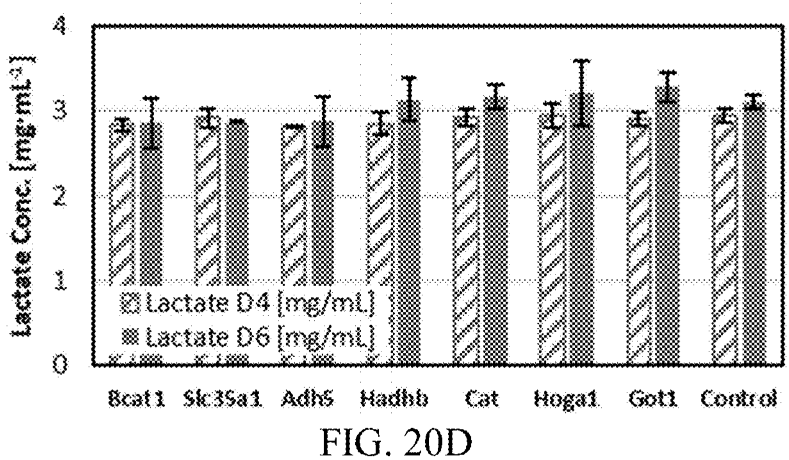
Figure 20E:
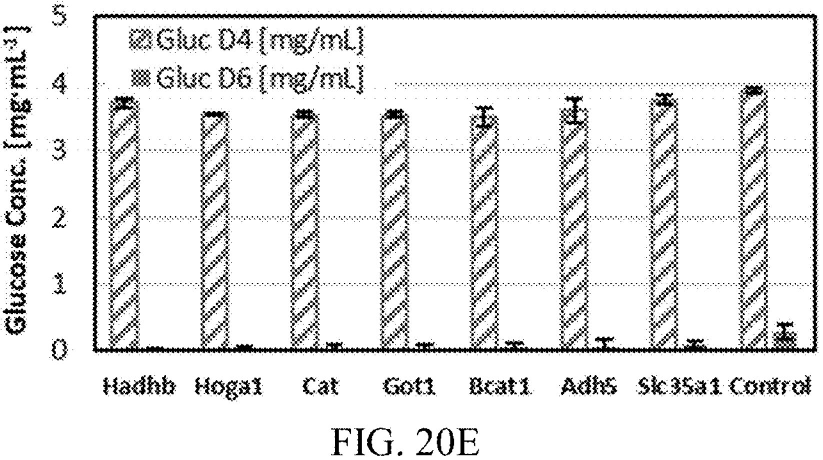
Figure 20F:
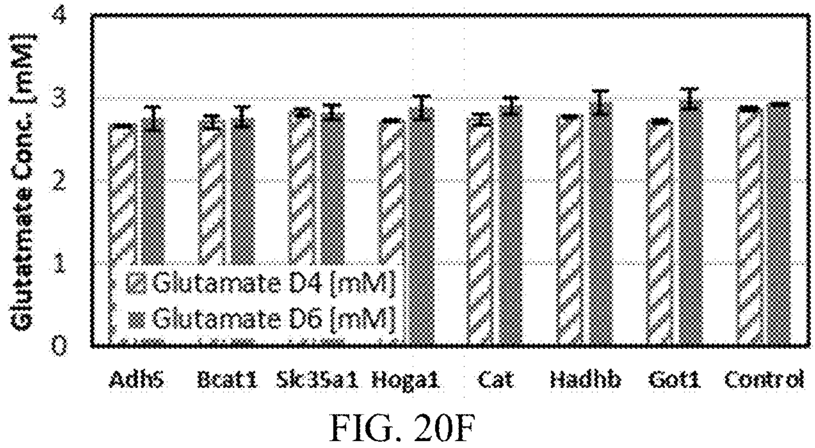
Figure 20G:
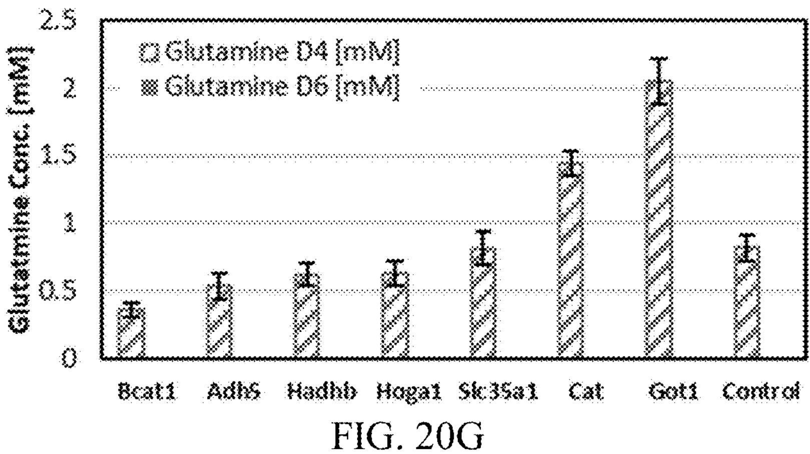
Figure 21A:
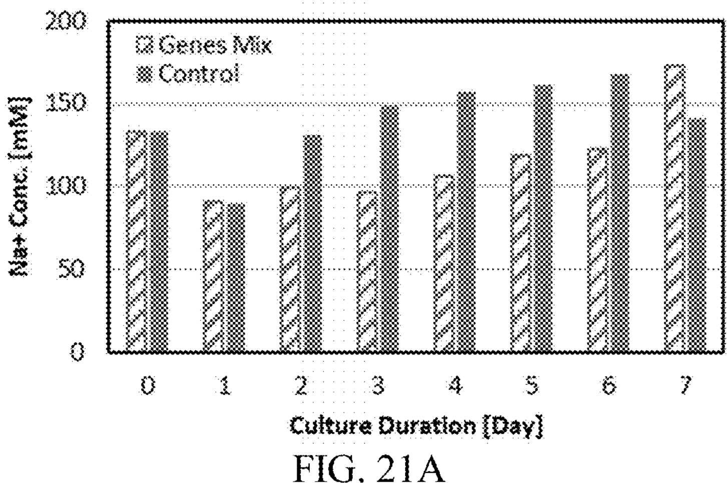
FIG. 21A-G are graphs showing the nutrient uptake profile of gene mix transfected subclones.
Figure 21B:
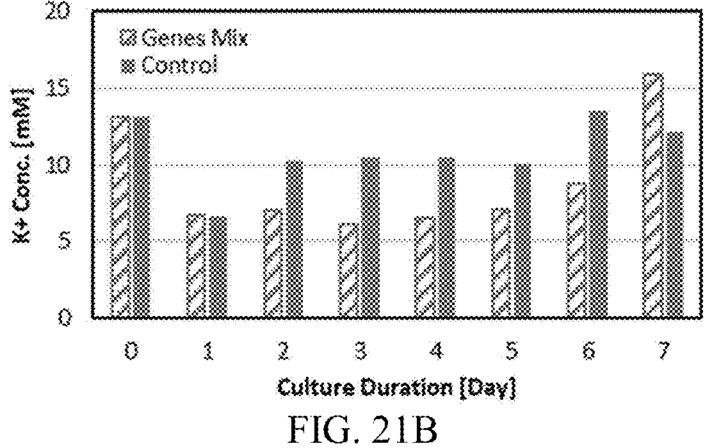
Figure 21C:
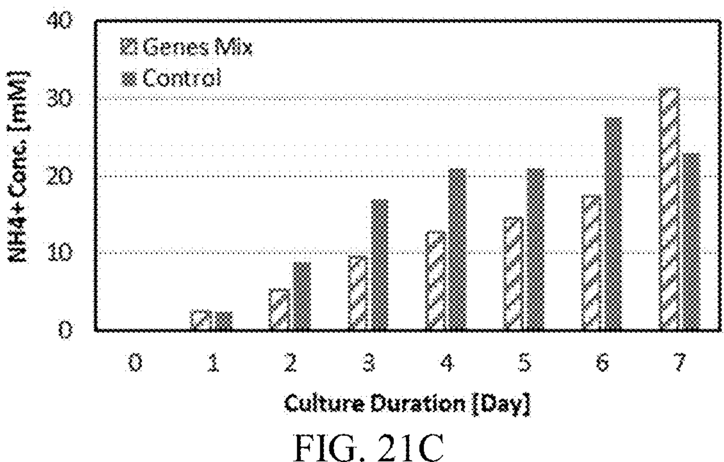
Figure 21D:
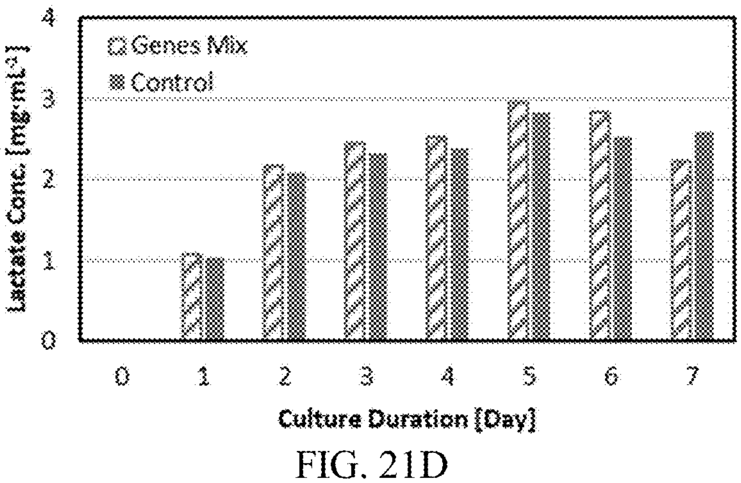
Figure 21E:
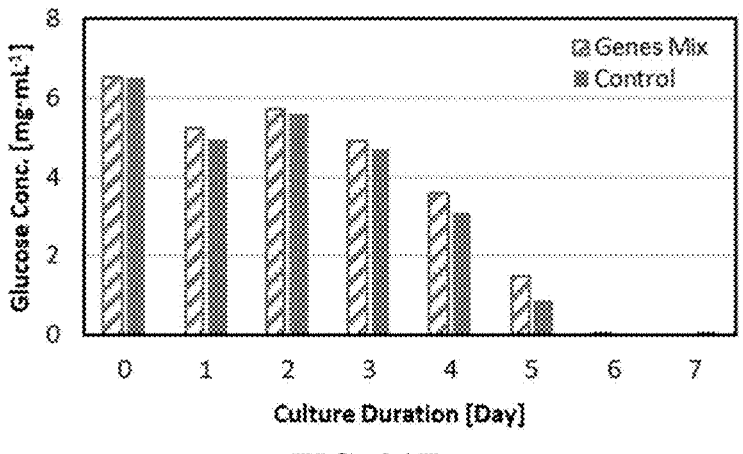
Figure 21F:
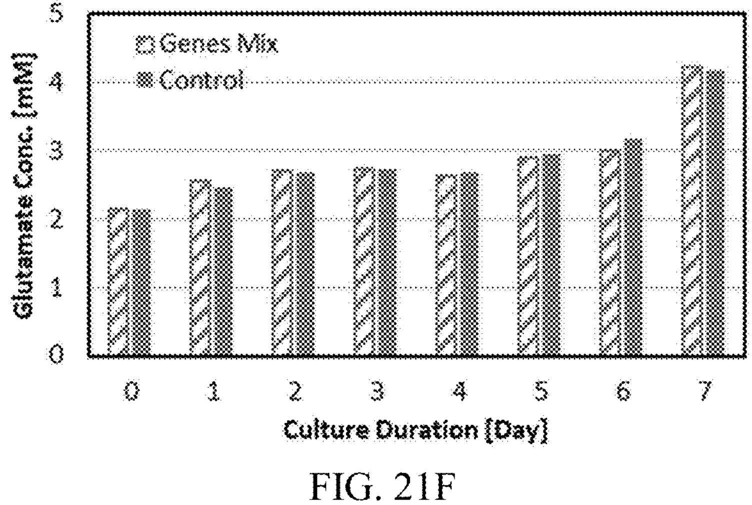
Figure 21G:
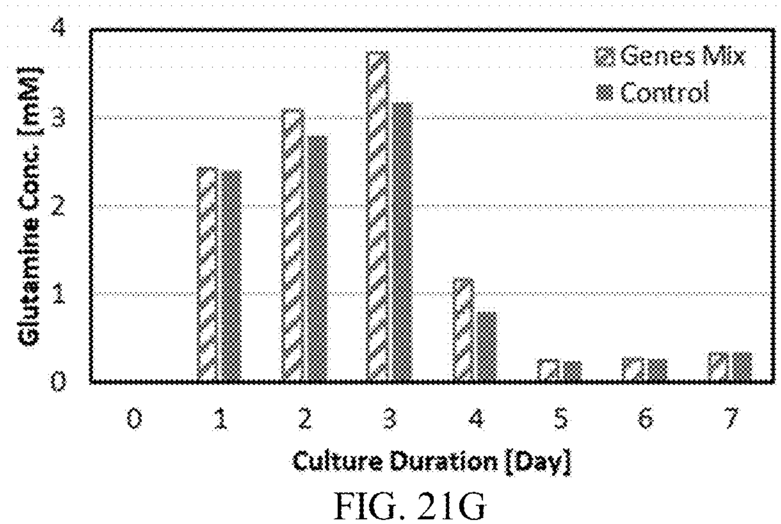

The nutrients consumption profile of the genes mix condition was also studied, as shown in FIG. 21A-G. Overall, the accumulated concentration of sodium and potassium measured throughout the entire culture duration is higher for the genes mix condition when comparing against the control (see FIGS. 21A and 21B), except on Day 7 where the sodium and potassium accumulation profile of the control condition was higher. The data agree with the trend observed from the growth profile, where the genes mix subclone achieved higher peak VCD and cumulative IVCD. It was speculated that higher cell density from the genes mix culture consume more sodium and potassium to maintain growth and other cellular activity, except until Day 7 where cell death occurred. Interestingly, the genes mix condition consumed less glutamine and glutamate (more accumulated glutamine and glutamate measured in the spent medium, FIGS. 21E and 21G), while less amount of ammonia and lactate (lower concentration of ammonia and lactate measured, as seen in FIGS. 21C and 21D) and maintained higher peak VCD and higher overall cumulative IVCD (FIGS. 19A and 19B). The data altogether suggests that when all seven genes are transfected to cells at the same time, the effect of the transfected genes were more significant, with studied condition consuming less nutrients which allow them to generate lesser amount of toxic growth by-products and inhibitory metabolites (see FIG. 17), allowing them to achieve a higher overall cell density and better cultural performance.

Conclusion

Mammalia cells are known to secrete growth inhibitory metabolites during growth and production phase, which hampers cellular performance and negatively impacts final productivity and product quality attributes. Eight growth inhibitors have been identified in a typical CHO and HEK 293 bioprocess. Seven of these genes (Adh5, Bcat1, Cat, Got1, Hadhb, Hoga1, and Slc35a1) were transfected into CHO cells to regulate their metabolism. The concentrations of metabolites measured through LC-MS/MS were successfully decreased by re-allocating cellular internal metabolic fluxes going into key metabolic pathways capable of direct or indirect metabolism of previously identified inhibitors. When the seven identified genes were individually transfected to cell at plasmid concentration of 8 $\mu g \cdot \mu L^{-1}$ per gene, peak cellular VCD and cumulative IVCD were improved when compared against the control throughout the entire culture duration, post transfection. The concentration of the inhibitory metabolites accumulated in the spent media, of each subclone, as measured through LC-MS/MS, was also lowered.

Each of the seven genes were also transfected together into cells at 6.25 $\mu g \cdot \mu L^{-1}$ per gene (a total of plasmid concentration of 43.75 $\mu g \cdot \mu L^{-1}$ for seven total genes). The results showed that improvement in cellular performance was also achieved, with the genes mix attaining higher peak VCD and cumulative IVCD. Interestingly, the effect of multi genes transfection appeared to have a more profound impact on cellular metabolism compared to single gene transfection. The study reveals that the genes mix condition showed less glutamine and glutamate being consumed (more accumulated glutamine and glutamate measured in the spent medium), which allowed cells to secrete less ammonia and lactate, while at the same time maintaining better growth profile and generating less growth inhibitory metabolites. All in all, the study successfully demonstrates that by coupling genome scale modeling with pathway analysis, the research elucidates a control strategy platform capable of mitigating the accumulation of metabolites by allocating metabolic fluxes into specific metabolic pathway capable of metabolizing growth inhibitors and promoting cellular growth.

The use of the terms “a” and “an” and “the” and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms “comprising”, “having”, “including”, and “containing” are to be construed as open-ended terms (i.e., meaning “including, but not limited to”) unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., “such as”), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of cell culture comprising (i) culturing mammalian cells in a cell culture medium, and (ii) maintaining at least one metabolite below an inhibitory concentration in the cell culture medium for the at least one metabolite by regulating enzyme expression to reduce synthesis of the at least one metabolite, wherein:

the at least one metabolite is at least one of aconitic acid (AA), leucinic acid (HICA), cytidine monophosphate (CMP), methylsuccinic acid (MSA), trigonelline (TRI), N-acetylputrescinium (NAP), or a combination thereof;

the enzyme to reduce the synthesis of HICA comprises at least one of alcohol dehydrogenase 5 (ADH5), branched-chain amino acid transaminase 1 (BCAT1), solute carrier family 35 member A1 (SLC35A1), glutamic oxaloacetic transaminase 1 (GOT1), hydroxyacyl-CoA dehydrogenase trifunctional multienzyme complex subunit beta (HADHB), or a combination thereof;

the enzyme to reduce the synthesis of CMP comprises at least one of ADH5, BCAT1, catalase (CAT), GOT1, 4-hydroxy-2-oxoglutarate aldolase 1 (HOGA1), SLC35A1, HADHB or a combination thereof;

the enzyme to reduce the synthesis of MSA comprises at least one of BCAT1, GOT1, HADHB, HOGA1, SLC35A1 or a combination thereof;

the enzyme to reduce the synthesis of TRI comprises at least one of BCAT1, GOT1, HADHB, CAT, HOGA1, SLC35A1, or a combination thereof;

the enzyme to reduce the synthesis of NAP comprises at least one of BCAT1, SLC35A1, HOGA1, GOT1, CAT, HADHB or a combination thereof; and the enzyme to reduce the synthesis of trans-aconitic acid comprises at least one of BCAT1, ADH5, GOT1, HOGA1, SLC35A1, HADHB, or a combination thereof, wherein the enzyme comprises ADH5 and BCAT1.

2. The method of claim 1, wherein the method further comprises measuring the concentration of the at least one metabolite, and when the measured concentration of the at least one metabolite is above a predefined value, regulating enzyme expression to reduce the synthesis of the at least one metabolite.

3. The method of claim 2, wherein regulating enzyme expression to reduce the synthesis of the at least one metabolite comprises adding a recombinant deoxyribonucleic acid (DNA) molecule to overexpress the enzyme, wherein the enzyme is a downstream enzyme.

4. The method of claim 1, wherein the mammalian cells are CHO cells or HEK 293 cells.

5. The method of claim 1, wherein the enzyme comprises ADH5, BCAT1, GOT1, HADHB, HOGA1, SLC35A1, and CAT.

6. The method of claim 1, wherein the concentration of the at least one metabolite is measured using at least one of nuclear magnetic resonance (NMR) spectroscopy, Raman spectroscopy, High/Ultra Performance Liquid Chromatography (H/UPLC), Liquid Chromatography Mass Spectrometer (LC-MS), Gas Chromatography Mass Spectrometer (GC-MS) technology, or a combination thereof.

7. The method of claim 1, wherein maintaining the at least one metabolite below an inhibitory concentration in the cell culture medium for the at least one metabolite comprises controlling at least one of temperature, dissolved oxygen level, pH, or a combination thereof.

8. The method of claim 1, wherein at least one of:

the mammalian cells are CHO cells, HEK 293 cells, HT-1080 cells, engineered T cells, or engineered natural killer cells;

the cell culture is a batch culture, a fed batch culture, or a perfusion culture; or a combination thereof.

9. The method of claim 1, wherein the mammalian cells express a recombinant protein, a gene product, or a cell product.

10. The method of claim 9, wherein the recombinant protein is a monoclonal antibody.

11. The method of claim 1, wherein cell growth and/or productivity are increased as compared to a control culture, wherein the control culture is identical to the culture of claim 1 except it is not cultured using step (ii).

12. The method of claim 11, wherein the cell growth is determined by maximum viable cell density and is increased by at least 5% as compared to the control culture.

13. The method of claim 1, wherein at least one of:

the at least one metabolite includes AA and concentration of AA in the cell culture medium is lower than 440 μM, the at least one metabolite includes HICA and concentration of HICA in the cell culture medium is lower than 23.5 μM, the at least one metabolite includes CMP and concentration of CMP in the cell culture medium is lower than 10 μM, the at least one metabolite includes MSA and concentration of MSA in the cell culture medium is lower than 3.75 μM, the at least one metabolite includes TRI and concentration of TRI in the cell culture medium is lower than 0.35 μM, the at least one metabolite includes NAP and concentration of NAP in the cell culture medium is lower than 0.3 μM, or a combination thereof.

14. The method of claim 13, wherein the concentration of the at least one metabolite is measured using at least one of nuclear magnetic resonance (NMR) spectroscopy, Raman spectroscopy, High/Ultra Performance Liquid Chromatography (H/UPLC), Liquid Chromatography Mass Spectrometer (LC-MS), Gas Chromatography Mass Spectrometer (GC-MS) technology, or a combination thereof.

15. The method of claim 1, wherein the enzyme further comprises at least one of GOT1, HADHB, HOGA1, SLC35A1, CAT, or a combination thereof.

16. A method of cell culture comprising (i) culturing mammalian cells in a cell culture medium, and (ii) maintaining at least one metabolite below an inhibitory concentration in the cell culture medium for the at least one metabolite by regulating enzyme expression to reduce synthesis of the at least one metabolite, wherein the at least one metabolite is at least one of aconitic acid (AA), leucinic acid (HICA), cytidine monophosphate (CMP), methylsuccinic acid (MSA), trigonelline (TRI), N-acetylputrescinium (NAP), or a combination thereof, and wherein the enzyme comprises alcohol dehydrogenase 5 (ADH5), branched-chain amino acid transaminase 1 (BCAT1), catalase (CAT), Glutamic oxaloacetic transaminase 1 (GOT1), Hydroxyacyl-CoA Dehydrogenase Trifunctional Multienzyme Complex Subunit Beta (HADHB), 4-hydroxy-2-oxoglutarate aldolase 1 (HOGA1), and solute carrier family 35 member A1 (SLC35A1).

17. The method of claim 16, further comprising measuring the concentration of the at least one metabolite, and when the measured concentration of the at least one metabolite is above a predefined value, regulating enzyme expression to reduce the synthesis of the at least one metabolite.

18. The method of claim 17, wherein regulating enzyme expression to reduce the synthesis of the at least one metabolite comprises adding a recombinant deoxyribonucleic acid (DNA) molecule to overexpress the enzyme, wherein the enzyme is a downstream enzyme.

19. The method of claim 16, wherein at least one of:

maintaining the at least one metabolite below an inhibitory concentration in the cell culture medium for the at least one metabolite comprises controlling at least one of temperature, dissolved oxygen level, pH, or a combination thereof;

the mammalian cells are CHO cells, HEK 293 cells, HT-1080 cells, engineered T cells, or engineered natural killer cells;

the cell culture is a batch culture, a fed batch culture, or a perfusion culture;

the cells express a recombinant protein, a gene product, or a cell product;

cell growth and/or productivity are increased as compared to a control culture, wherein the control culture is identical to the culture of claim 1 except it is not cultured using step (ii); or a combination thereof.

20. The method of claim 16, wherein at least one of:

the at least one metabolite includes AA and concentration of AA in the cell culture medium is lower than 440 μM, the at least one metabolite includes HICA and concentration of HICA in the cell culture medium is lower than 23.5 μM, the at least one metabolite includes CMP and concentration of CMP in the cell culture medium is lower than 10 μM, the at least one metabolite includes MSA and concentration of MSA in the cell culture medium is lower than 3.75 μM, the at least one metabolite includes TRI and concentration of TRI in the cell culture medium is lower than 0.35 μM, the at least one metabolite includes NAP and concentration of NAP in the cell culture medium is lower than 0.3 μM, or a combination thereof.

* * * * *